(12) United States Patent
Skarsgard

(10) Patent No.: US 12,268,597 B2
(45) Date of Patent: Apr. 8, 2025

(54) APPARATUS FOR USE IN REPLACING MITRAL VALVES AND METHODS OF USE THEREOF

(71) Applicant: Vesalius Cardiovascular Inc., Vancouver (CA)

(72) Inventor: Peter Skarsgard, Vancouver (CA)

(73) Assignee: VESALIUS CARDIOVASCULAR INC., Vancouver (CA)

( * ) Notice: Subject to any disclaimer, the term of this patent is extended or adjusted under 35 U.S.C. 154(b) by 1142 days.

(21) Appl. No.: 16/970,610

(22) PCT Filed: Feb. 19, 2019

(86) PCT No.: PCT/CA2019/050199
§ 371 (c)(1),
(2) Date: Aug. 17, 2020

(87) PCT Pub. No.: WO2019/157604
PCT Pub. Date: Aug. 22, 2019

(65) Prior Publication Data
US 2021/0085456 A1 Mar. 25, 2021

Related U.S. Application Data

(60) Provisional application No. 62/641,148, filed on Mar. 9, 2018, provisional application No. 62/632,198, filed on Feb. 19, 2018.

(51) Int. Cl.
*A61B 17/00* (2006.01)
*A61B 17/3207* (2006.01)
(Continued)

(52) U.S. Cl.
CPC ...... *A61F 2/2427* (2013.01); *A61B 17/00234* (2013.01); *A61B 17/320725* (2013.01);
(Continued)

(58) Field of Classification Search
CPC ............. A61F 2/2427; A61B 17/00234; A61B 17/320725; A61B 17/3423;
(Continued)

(56) References Cited

U.S. PATENT DOCUMENTS 6,752,813 B2 6/2004 Goldfarb et al.
7,854,755 B2 12/2010 Lafontaine et al.
(Continued)

FOREIGN PATENT DOCUMENTS

CA 2777067 A1 4/2011
EP 2399527 A1 12/2011
(Continued)

*Primary Examiner* — Ashley L Fishback
(74) *Attorney, Agent, or Firm* — Oyen Wiggs Green & Mutala LLP

(57) ABSTRACT

Apparatus and methods for replacing a mitral valve are provided. The apparatus comprises controller, a cutting section movable between a collapsed position for delivering the apparatus to a mitral valve and an expanded position for incising a mitral valve leaflet, and a guidewire. The apparatus is sized and dimensioned to enter a subject through a first access site, traverse through a subject's circulatory system, and exit the subject through a second access site so that a distal end of the guidewire and the controller are external to the subject's circulatory system when the apparatus is situated intravascularly. The method comprises inserting the apparatus percutaneously through the first access site, advancing the apparatus through the subject's circulatory system, advancing the apparatus through the second access site, incising a mitral valve leaflet, and delivering a prosthetic valve intravascularly over the guidewire to the incised mitral valve leaflet from the second access site.

15 Claims, 32 Drawing Sheets

(51) Int. Cl.
*A61B 17/34* (2006.01)
*A61F 2/24* (2006.01)
(52) U.S. Cl.
CPC .................. *A61B 17/3423* (2013.01); *A61B 2017/00243* (2013.01); *A61B 2017/00358* (2013.01); *A61B 2017/3425* (2013.01)
(58) Field of Classification Search
CPC ........... A61B 2017/00243; A61B 2017/00358; A61B 2017/3425
See application file for complete search history.

(56) References Cited

U.S. PATENT DOCUMENTS

| | | | |
|---|---|---|---|
| 8,444,689 B2 | 5/2013 | Zhang | |
| 8,979,922 B2 | 3/2015 | Jayasinghe et al. | |
| 9,119,651 B2 | 9/2015 | Katoh et al. | |
| 9,387,064 B2 | 7/2016 | Kohl et al. | |
| 2002/0107531 A1 | 8/2002 | Schreck et al. | |
| 2004/0034380 A1 | 2/2004 | Woolfson et al. | |
| 2009/0306582 A1 | 12/2009 | Granada et al. | |
| 2013/0116715 A1 | 5/2013 | Weber | |
| 2014/0155924 A1 | 6/2014 | McDonald | |
| 2015/0257883 A1 | 9/2015 | Basude et al. | |
| 2015/0359556 A1 | 12/2015 | Vardi | |
| 2017/0273787 A1 | 9/2017 | Passman et al. | |
| 2018/0000509 A1 | 1/2018 | Wilson et al. | |

FOREIGN PATENT DOCUMENTS

| | | |
|---|---|---|
| WO | 8204388 A1 | 12/1982 |
| WO | 03088809 A2 | 10/2003 |
| WO | 2011047168 A1 | 4/2011 |
| WO | 2011163322 A1 | 12/2011 |
| WO | 2014106847 A1 | 7/2014 |

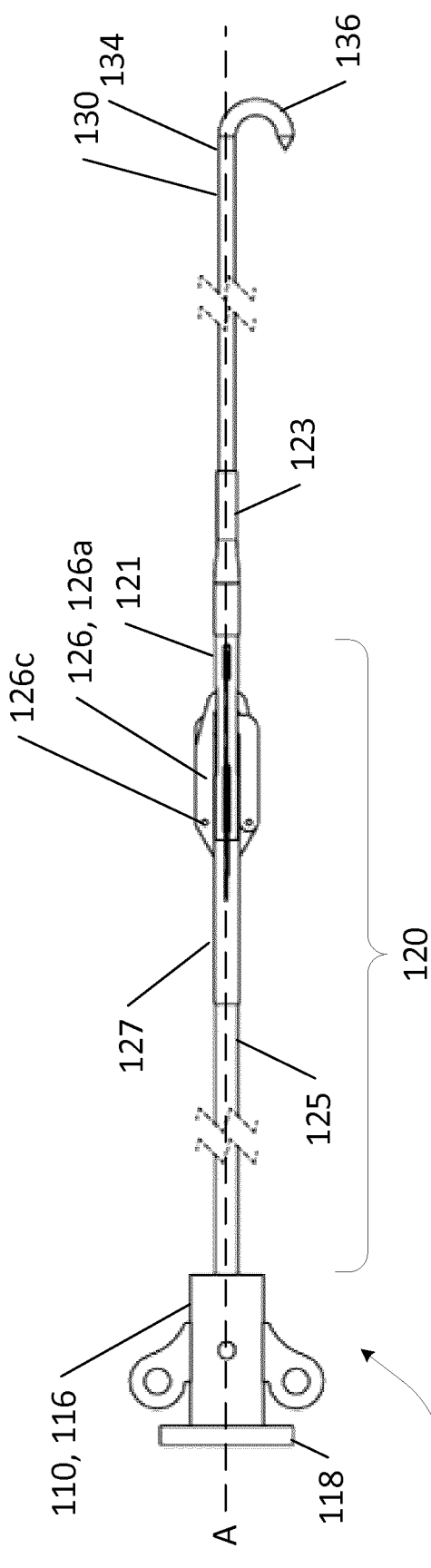
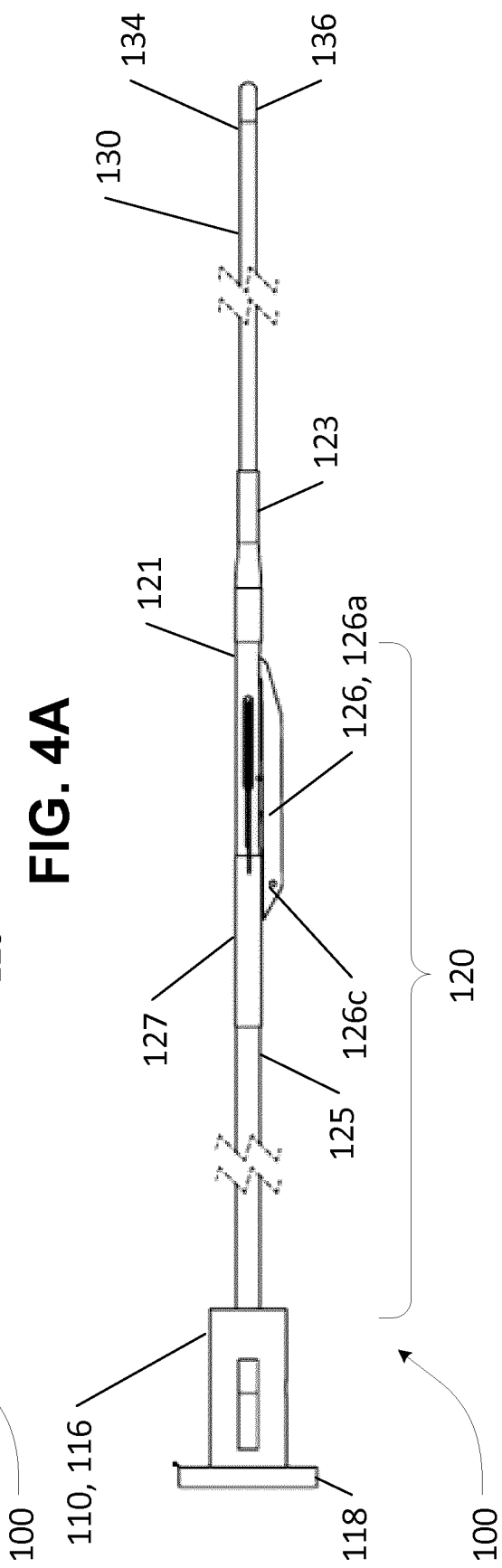
FIG. 4A
FIG. 4B

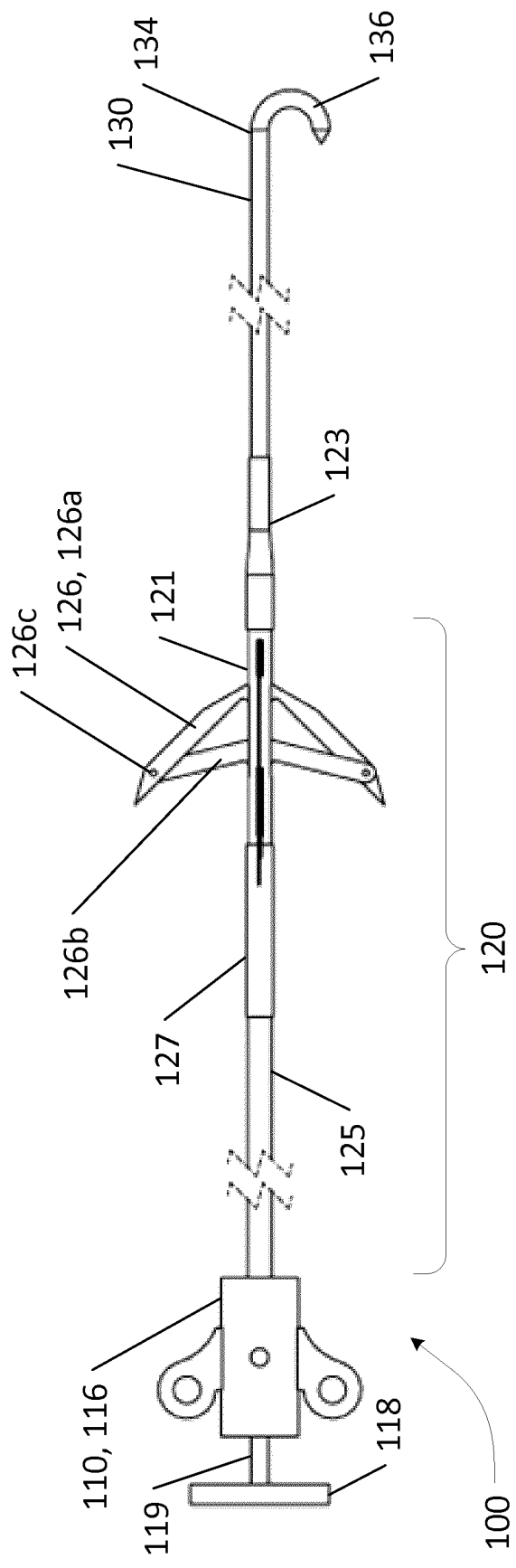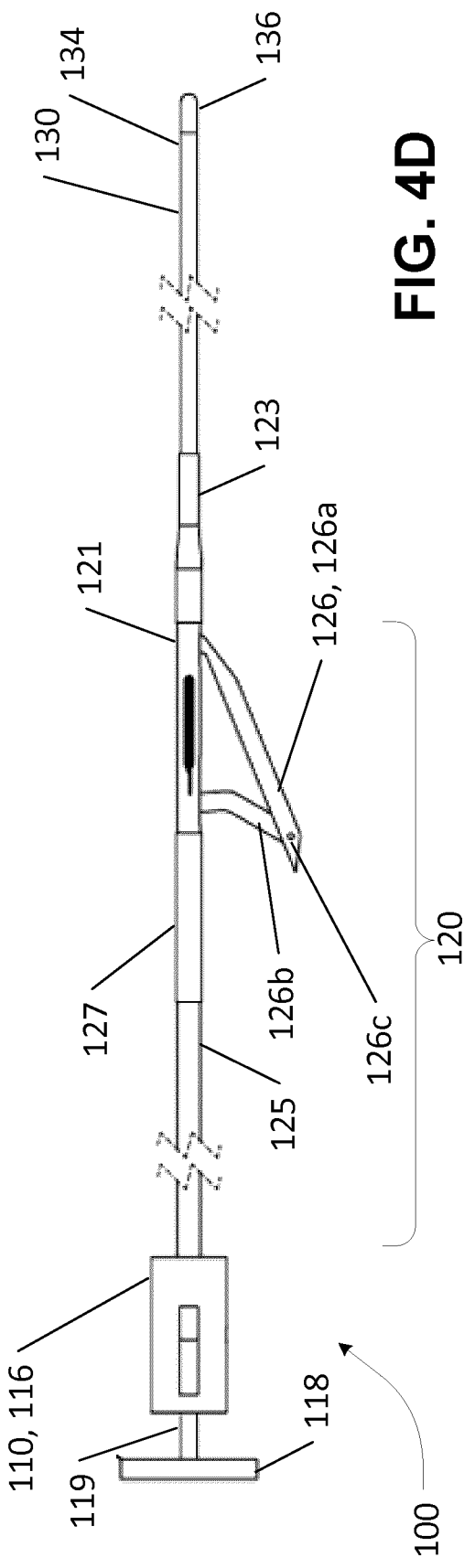
FIG. 4C
FIG. 4D

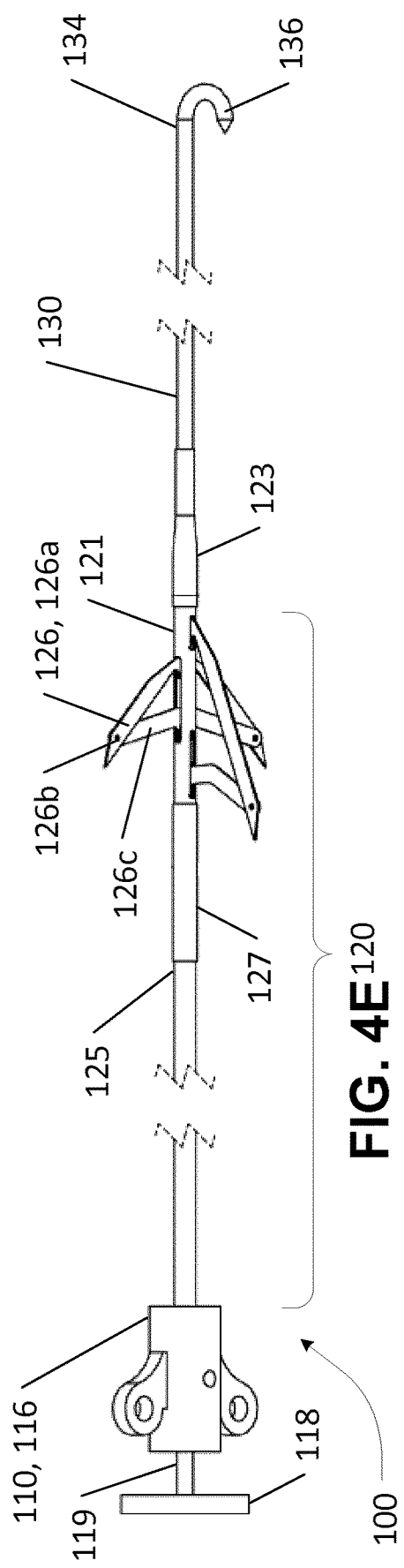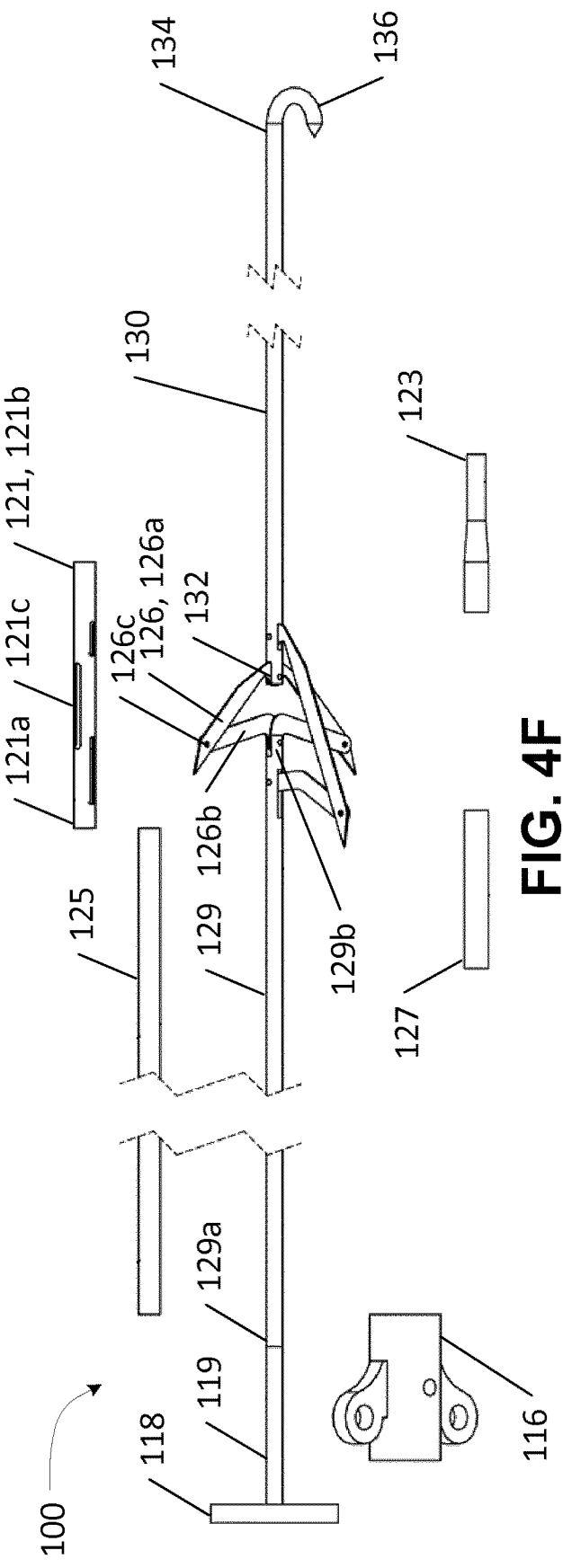

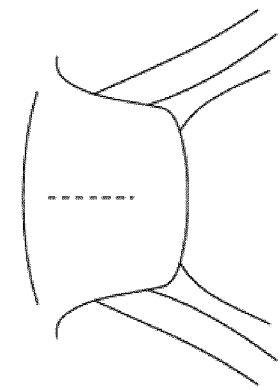
FIG. 6C
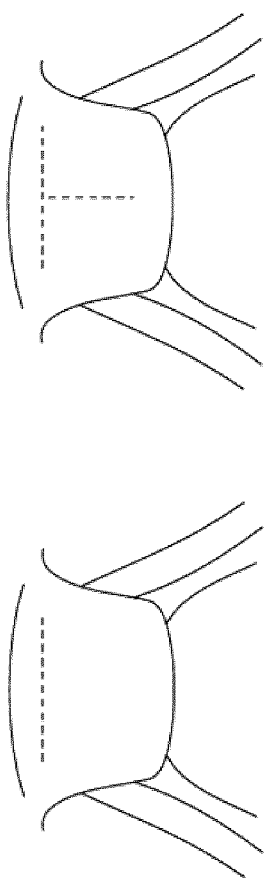
FIG. 6B
FIG. 6A
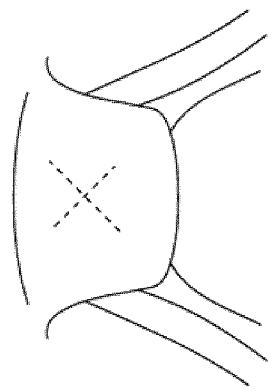
FIG. 6E
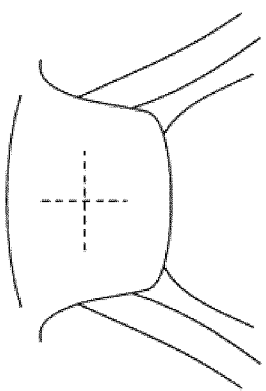
FIG. 6D

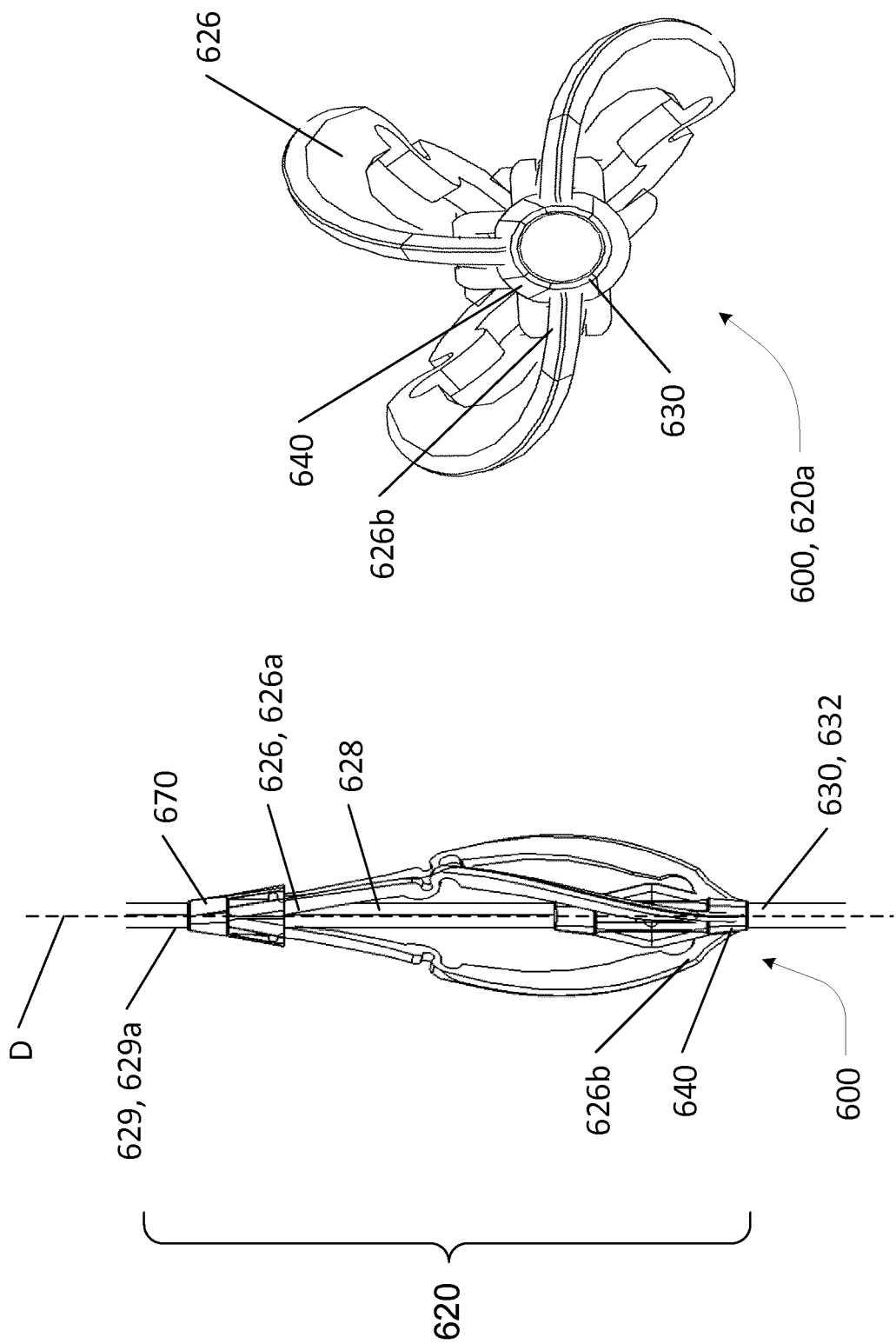

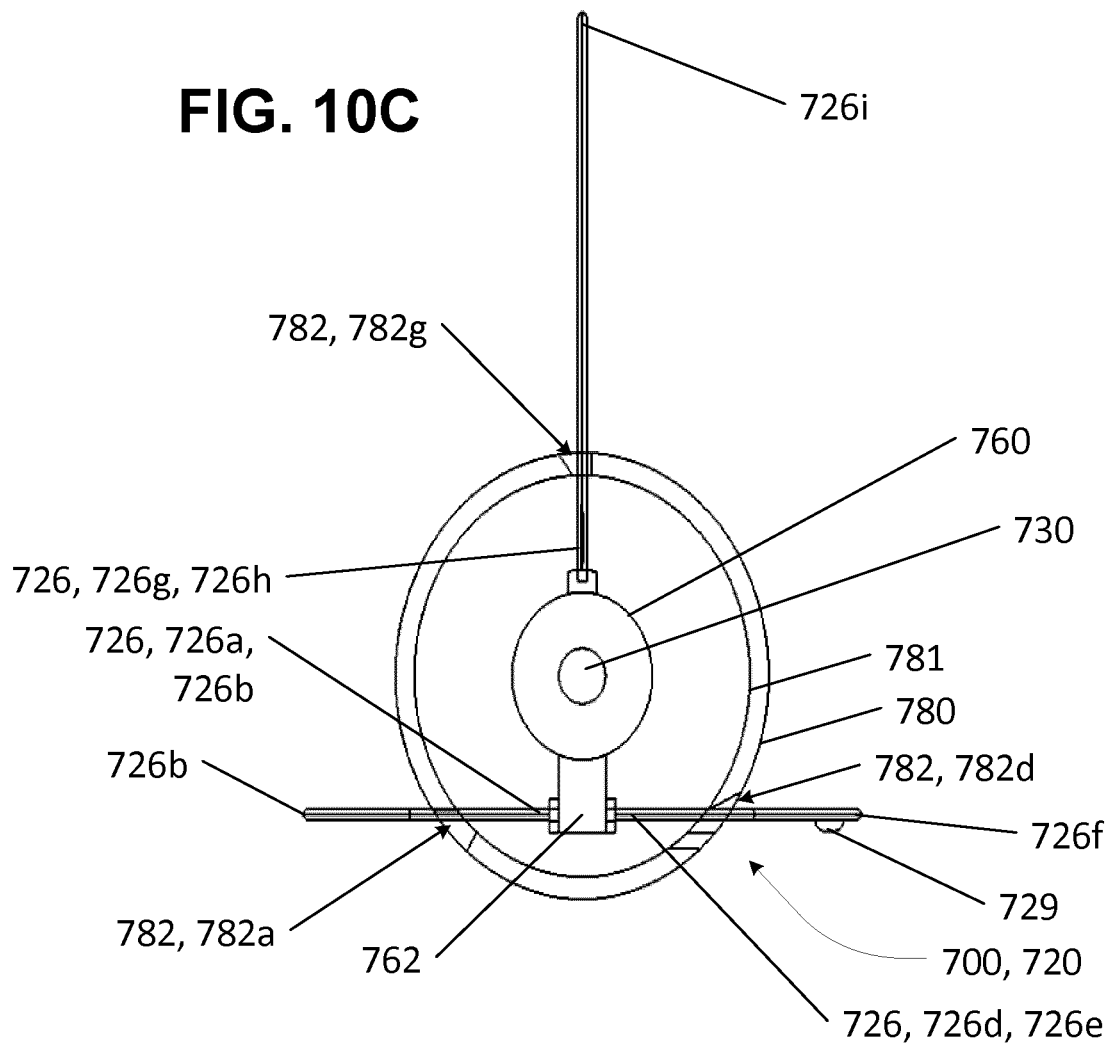

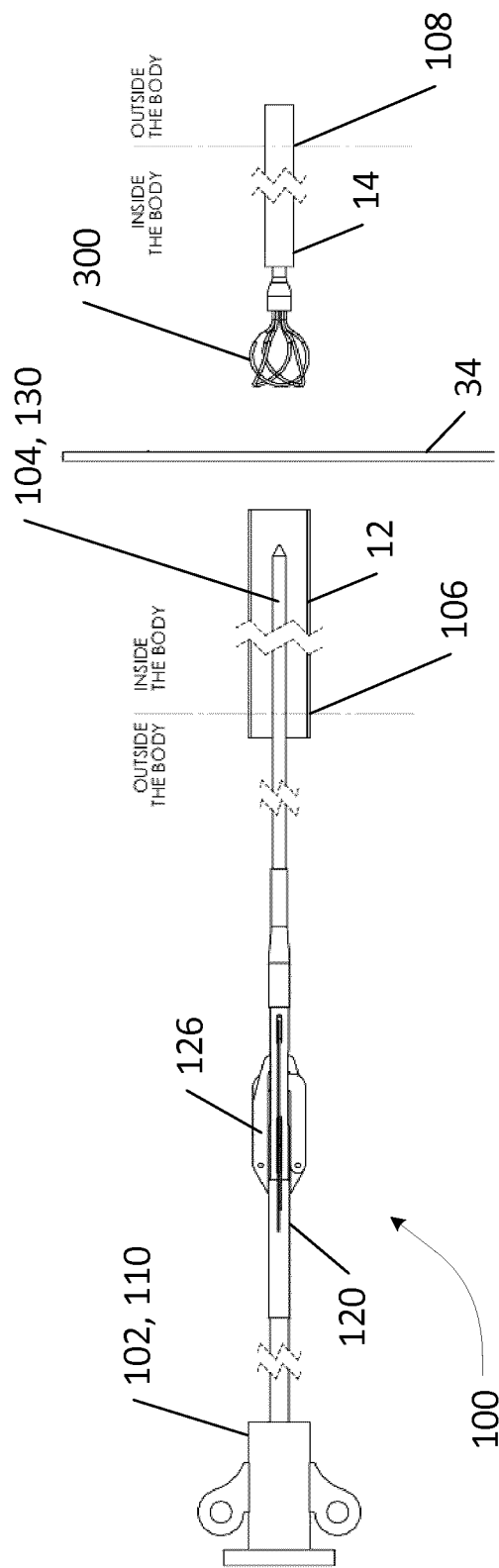
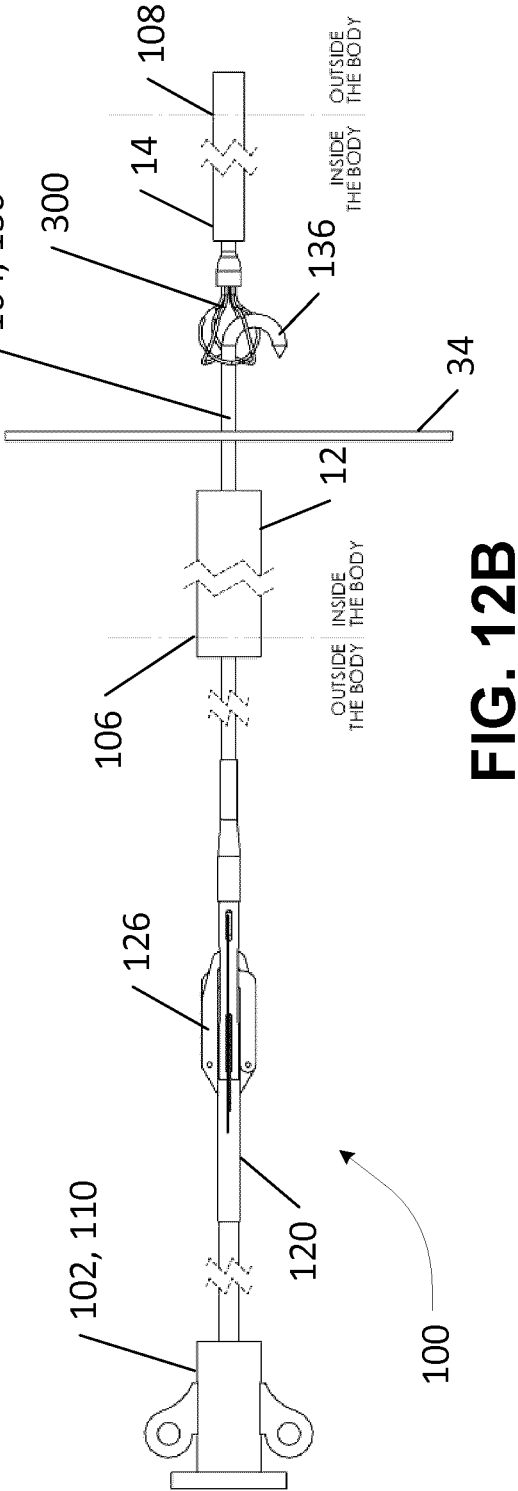
FIG. 12A
FIG. 12B

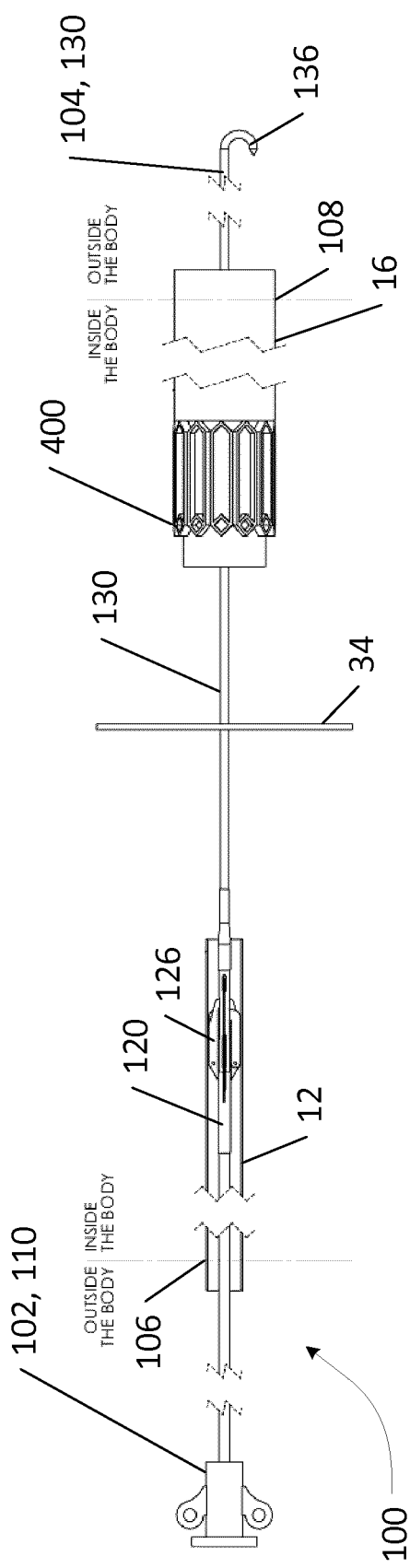
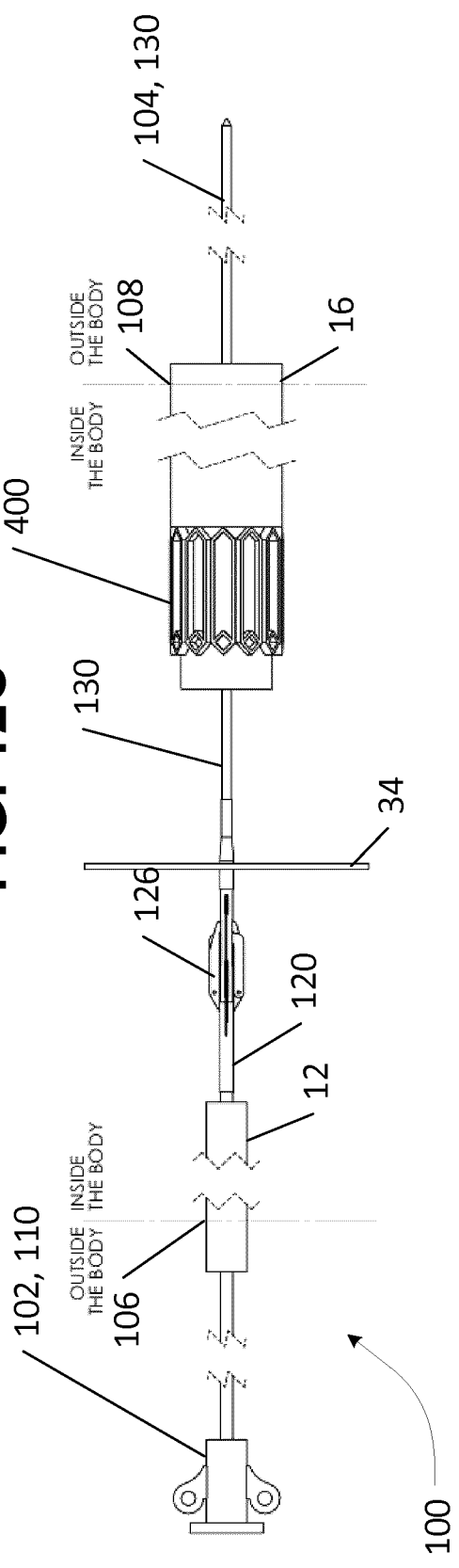
FIG. 12C
FIG. 12D

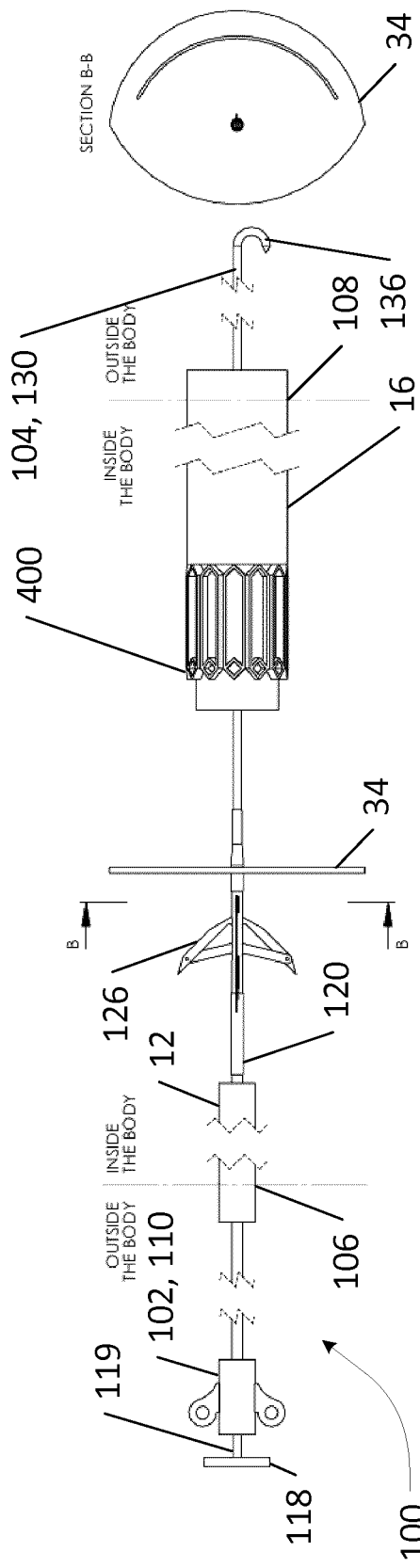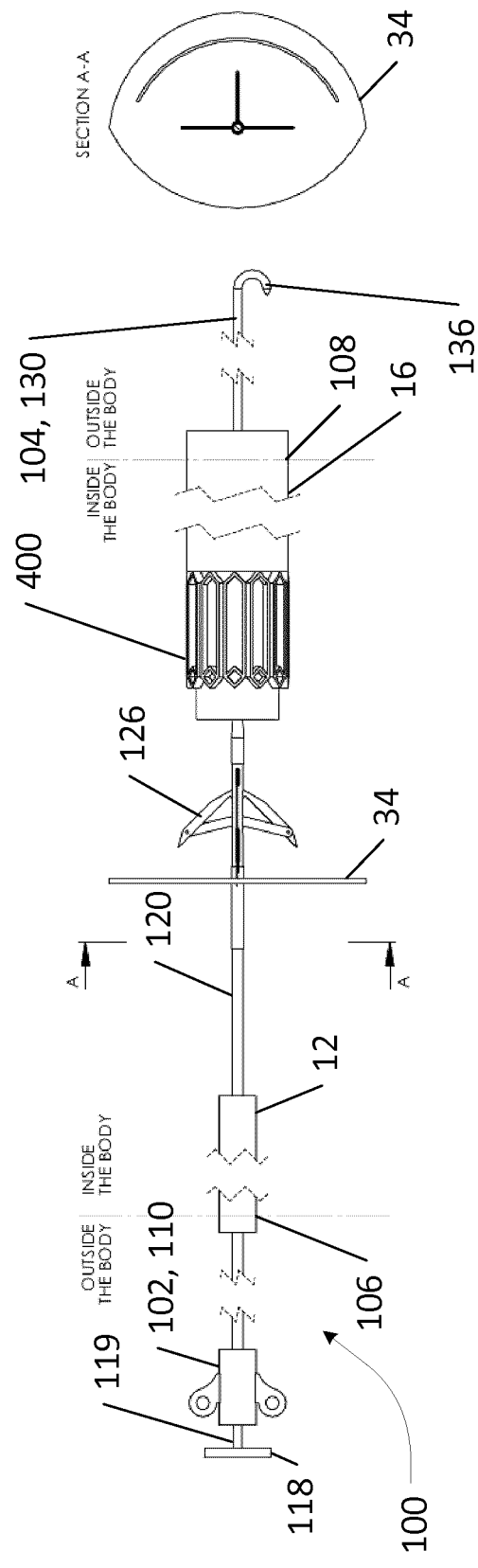

APPARATUS FOR USE IN REPLACING MITRAL VALVES AND METHODS OF USE THEREOF

CROSS-REFERENCE TO RELATED APPLICATIONS

This application is a 371 national phase entry of Patent Cooperation Treaty application No. PCT/CA2019/050199 filed Feb. 19, 2019, which claims priority to U.S. Provisional Application No. 62/632,198 filed Feb. 19, 2018 and U.S. Provisional Application No. 62/641,148 filed Mar. 9, 2018. These patent applications are herein incorporated by reference in their entirety, including without limitation, the specification, claims, and abstract, as well as any figures, tables, or drawings thereof.

TECHNICAL FIELD

The present invention relates to apparatus for use in replacing heart valves and methods of use thereof. In particular, the present invention relates to apparatus for use in replacing mitral valves and methods of use thereof.

BACKGROUND

The mitral valve is the most complex of the human heart's valves and is commonly associated with disease. Conditions affecting the normal functioning of the mitral valve include, for example, mitral valve regurgitation, mitral valve prolapse, and mitral valve stenosis. Mitral valve regurgitation refers to the condition whereby the leaflets of the mitral valve fail to coapt into apposition during ventricular contraction, resulting in abnormal leaking of blood from the left ventricle into the left atrium. Mitral valve prolapse refers to the condition where the mitral valve leaflets bulge abnormally up into the left atrium causing irregular behaviour of the mitral valve. Mitral valve stenosis refers to the narrowing of the heart's mitral valve obstructing blood flow. A number of factors may affect the normal functioning of the mitral valve leaflets.

Although intermediate grades of impaired functioning of the mitral valve may not require treatment, severely impaired mitral valve function may result in symptoms (for example, breathlessness, fatigue, exercise intolerance), and may represent a threat to life expectancy. Often, invasive surgery must be performed to repair or replace an abnormal mitral valve.

Traditionally, repairing or replacing a mitral valve involves an open heart procedure. Open heart procedures present subjects with morbidity and mortality risks and require a post-op period of convalescence that is typically several months in duration. Open heart surgery may pose prohibitive risks, or may otherwise not be ideal for some subjects, including some elderly subjects and subjects with other health issues. Repairing or replacing the mitral valve without invasive open heart procedures may be attractive therapy for such subjects.

Transcatheter mitral valve replacement (TMVR) apparatus and methods for treating mitral regurgitation in subjects at high or prohibitive surgical risks are known. Traditional TMVR technologies use anchoring features to securely attach a prosthetic mitral valve to the native mitral valve. The replacement valves often cause left ventricular outflow tract (LVOT) obstruction. LVOT obstruction occurs when the replacement valve pushes the anterior leaflet of the mitral valve underneath the aortic (i.e. outflow) valve, and against the ventricular septum. Further, successful implantation of such devices is complicated by the distinct structure and functioning of the mitral valve. A heart 2 showing LVOT obstruction is shown in FIG. 1. A conventional TMVR apparatus 4 pushes anterior mitral valve leaflet 6 under aortic valve 8 obstructing outflow.

While there has been some success in developing replacement heart valve prosthetics for percutaneous catheter-based delivery, such methods have not been particularly successfully applied to mitral valve replacement. Mitral valve replacement is complicated by the anatomy of the mitral valve, and particularly that of the mitral valve annulus in which the mitral valve leaflets are located. The mitral valve annulus is typically of unpredictable and non-uniform configuration, as compared to the relatively uniform aortic valve annulus. The unpredictable anatomy of the mitral valve annulus complicates safe, stable, and meticulous deployment of mitral valve prostheses. Transcatheter aortic valves for treating mitral regurgitation are known, and can be implanted when a suitable docking device (e.g. a surgically placed mitral annular ring) is present on the mitral valve. However, transcatheter aortic valves can suffer from similar complications as a TMVR apparatus, including LVOT obstruction when the replacement valve pushes the anterior mitral valve leaflet underneath the aortic valve.

Some mitral valve replacement techniques involve the division or incision of the native valve prior to positioning and implanting the mitral valve prosthesis. This is a challenging technique associated with potentially fatal complications if the mitral valve prosthesis is not precisely positioned and/or the mitral valve prosthesis is not implanted at least closely or immediately following the division or incision of the native valve.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Some aspects of the present invention provide an apparatus for use in mitral valve replacement comprising a controller, a cutting section movable between a collapsed position for delivering the apparatus to a mitral valve and an expanded position for incising a mitral valve leaflet, and a guidewire. The apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly.

In some embodiments a proximal end of the guidewire extends longitudinally from a distal end of the cutting section.

In some embodiments a proximal end of the cutting section extends longitudinally from a distal end of the controller.

In some embodiments the cutting section defines a lumen extending longitudinally through the cutting section and the guidewire extends through and is slideable within the cutting section.

In some embodiments the cutting section comprises at least one blade configured to radially extend away from a longitudinal axis defined by the apparatus in the expanded position and radially collapse toward the longitudinal axis in the collapsed position.

In some embodiments each blade is formed from a memory material.

In some embodiments the memory material comprises a memory metal alloy from the group consisting of one or more of stainless steel, nickel, titanium, and nitinol.

In some embodiments the blade retains a pre-deformed shape in the expanded position and is deformable into a deformed shape in the collapsed position.

In some embodiments each blade comprises a cutting blade pivotally coupled at a proximal end to a distal end of a lever arm, each cutting blade pivotally coupled at a distal end to the proximal end of the guidewire and each lever arm pivotally coupled at a proximal end to the controller.

In some embodiments the distance between the distal end of the cutting blade and the proximal end of the lever arm is greater in the collapsed position than in the expanded position.

In some embodiments the cutting section comprises a rod and a runner longitudinally slidable about the rod.

In some embodiments each blade comprises a distal end pivotally coupled to a distal section of the rod and a proximal end pivotally coupled to the runner.

In some embodiments the distance between the proximal and distal ends of each blade is greater in the collapsed position than in the expanded position.

In some embodiments the runner is rotatable about the rod to rotate each blade about the longitudinal axis.

In some embodiments a radial cross-sectional area of the cutting section is reduced by rotating each blade about the longitudinal axis in a first direction.

In some embodiments the radial cross-sectional area of the cutting section is increased by rotating each blade about the longitudinal axis in a second direction opposed to the first direction.

In some embodiments the cutting section comprises a rotator housed within a case defining one or more slots configured to receive the at least one blade.

In some embodiments each blade extends radially from the rotator and wraps concentrically about an inside surface of the case in the collapsed position.

In some embodiments each blade is expandable and retractable within the slot.

In some embodiments each blade extends radially from the rotator through the slot in the expanded position.

In some embodiments the cutting section is configured to incise the mitral valve leaflet with a predetermined pattern.

In some embodiments the predetermined pattern is selected from the group consisting of: a T-shaped incision, a linear incision, and an X-shaped incision.

In some embodiments the at least one blade extends radially away from a longitudinal axis defined by the apparatus and in a configuration that corresponds to the predetermined pattern.

In some embodiments the controller is configured to move the cutting section from the collapsed position to the expanded position and vice versa.

Another aspect of the present invention provides a method for replacing a mitral valve. The method comprises inserting an apparatus percutaneously through a first access site of a subject, advancing the apparatus intravascularly through the subject's circulatory system, and advancing the apparatus through a second access site of the subject. The apparatus comprises a controller, a cutting section, and a guidewire and the apparatus is sized and dimensioned to traverse the subject's circulatory system from the first access site to the second access site such that a distal end of the guidewire and the controller are external to the subject's body when the apparatus is situated intravascularly. The method further comprises incising a mitral valve leaflet using the cutting section and delivering a prosthetic valve intravascularly to the incised mitral valve leaflet from the second access site using the guidewire.

In some embodiments incising the mitral valve leaflet comprises expanding the cutting section from a collapsed position into an expanded position and advancing the cutting section in the expanded position through the mitral valve leaflet.

In some embodiments the method further comprises positioning the prosthetic valve into the incised mitral valve leaflet following incision.

In some embodiments the method further comprises positioning the prosthetic valve into the incised mitral valve leaflet immediately following incision.

In some embodiments the method comprises positioning the prosthetic valve into the incised mitral valve leaflet within less than about 5 seconds following incision.

In some embodiments the method comprises positioning the prosthetic valve into the incised mitral valve leaflet within less than about 3 seconds following incision.

In some embodiments the method comprises positioning the prosthetic valve into the incised mitral valve leaflet within less than about 1 second following incision.

In some embodiments the method comprises incising the mitral valve leaflet and implanting the prosthetic valve at a predetermined location determined using Transesophageal Echocardiography (TEE) and/or fluoroscopy techniques.

In some embodiments the predetermined location is selected to minimize or eliminate anterior displacement of the anterior leaflet.

In some embodiments the predetermined location is along a central axis of the anterior leaflet at a position away from the anterior annulus so that an adequate amount of anterior leaflet tissue is available for hemostatic implantation of the prosthesis within a docking device.

In some embodiment the predetermined location is selected to minimize or eliminate left ventricular outflow tract (LVOT) obstruction.

In some embodiments inserting the apparatus through the first access site and advancing the apparatus through the subject's circulatory system comprises using a retrograde transcatheter approach.

In some embodiments inserting the apparatus through the first access site and advancing the apparatus through the subject's circulatory system comprises using an antegrade transcatheter approach.

In some embodiments advancing the apparatus through the second access site comprises inserting and advancing a snaring guidewire percutaneously through the second access site, snaring the distal end of the apparatus intravascularly, and withdrawing the distal end of the apparatus through the second access site.

Another aspect of the present invention provides an apparatus for performing a method for replacing a mitral valve. The apparatus comprises a controller, a cutting section movable between a collapsed position for delivering the apparatus to a mitral valve and an expanded position for incising a mitral valve leaflet, and a guidewire. The apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly.

In some embodiments a proximal end of the guidewire extends longitudinally from a distal end of the cutting section.

In some embodiments a proximal end of the cutting section extends longitudinally from a distal end of the controller.

In some embodiments the cutting section defines a lumen extending longitudinally through the cutting section and the guidewire extends through and is slideable within the cutting section.

In some embodiments the cutting section comprises at least one blade configured to radially extend away from a longitudinal axis defined by the apparatus in the expanded position and radially collapse toward the longitudinal axis in the collapsed position.

In some embodiments each blade is formed from a memory material.

In some embodiments the memory material comprises a memory metal alloy from the group consisting of one or more of stainless steel, nickel, titanium, and nitinol.

In some embodiments the blade retains a pre-deformed shape in the expanded position and is deformable into a deformed shape in the collapsed position.

In some embodiments each blade comprises a cutting blade pivotally coupled at a proximal end to a distal end of a lever arm, each cutting blade pivotally coupled at a distal end to the proximal end of the guidewire and each lever arm pivotally coupled at a proximal end to the controller.

In some embodiments the distance between the distal end of the cutting blade and the proximal end of the lever arm is greater in the collapsed position than in the expanded position.

In some embodiments the cutting section comprises a rod and a runner longitudinally slidable about the rod.

In some embodiments each blade comprises a distal end pivotally coupled to a distal section of the rod and a proximal end pivotally coupled to the runner.

In some embodiments the distance between the proximal and distal ends of each blade is greater in the collapsed position than in the expanded position.

In some embodiments the runner is rotatable about the rod to rotate each blade about the longitudinal axis.

In some embodiments a radial cross-sectional area of the cutting section is reduced by rotating each blade about the longitudinal axis in a first direction.

In some embodiments the radial cross-sectional area of the cutting section is increased by rotating each blade about the longitudinal axis in a second direction opposed to the first direction.

In some embodiments the cutting section comprises a rotator housed within a case defining one or more slots configured to receive the at least one blade.

In some embodiments each blade extends radially from the rotator and wraps concentrically about an inside surface of the case in the collapsed position.

In some embodiments each blade is expandable and retractable within the slot.

In some embodiments each blade extends radially from the rotator through the slot in the expanded position.

In some embodiments the cutting section is configured to incise the mitral valve leaflet with a predetermined pattern.

In some embodiments the predetermined pattern is selected from the group consisting of: a T-shaped incision, a linear incision, and an X-shaped incision.

In some embodiments the at least one blade extends radially away from a longitudinal axis defined by the apparatus and in a configuration that corresponds to the predetermined pattern.

In some embodiments the controller is configured to move the cutting section from the collapsed position to the expanded position and vice versa.

Another aspect of the present invention provides a system for use in a mitral valve replacement. The system comprises a subaortic introducer and an apparatus comprising a controller, a cutting section movable between a collapsed position for delivering the apparatus to a mitral valve and an expanded position for incising a mitral valve leaflet, and a guidewire. The apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly.

In some embodiments the subaortic introducer comprises a destructible tip that maintains the guidewire in a linear position as the apparatus is advanced through a subject's circulatory system and permits the guidewire to deform in a J-shaped position as the apparatus destructs and is advanced through the tip.

In some embodiments a proximal end of the guidewire extends longitudinally from a distal end of the cutting section.

In some embodiments a proximal end of the cutting section extends longitudinally from a distal end of the controller.

In some embodiments the cutting section defines a lumen extending longitudinally through the cutting section and the guidewire extends through and is slideable within the cutting section.

In some embodiments the cutting section comprises at least one blade configured to radially extend away from a longitudinal axis defined the apparatus in the expanded position and radially collapse toward the longitudinal axis in the collapsed position.

In some embodiments each blade is formed from a memory material.

In some embodiments the memory material comprises a memory metal alloy from the group consisting of one or more of stainless steel, nickel, titanium, and nitinol.

In some embodiments the blade retains a pre-deformed shape in the expanded position and is deformable into a deformed shape in the collapsed position.

In some embodiments each blade comprises a cutting blade pivotally coupled at a proximal end to a distal end of a lever arm, each cutting blade pivotally coupled at a distal end to the proximal end of the guidewire and each lever arm pivotally coupled at a proximal end to the controller.

In some embodiments the distance between the distal end of the cutting blade and the proximal end of the lever arm is greater in the collapsed position than in the expanded position.

In some embodiments the cutting section comprises a rod and a runner longitudinally slidable about the rod.

In some embodiments each blade comprises a distal end pivotally coupled to a distal section of the rod and a proximal end pivotally coupled to the runner.

In some embodiments the distance between the proximal and distal ends of each blade is greater in the collapsed position than in the expanded position.

In some embodiments the runner is rotatable about the rod to rotate each blade about the longitudinal axis.

In some embodiments a radial cross-sectional area of the cutting section is reduced by rotating each blade about the longitudinal axis in a first direction.

In some embodiments the radial cross-sectional area of the cutting section is increased by rotating each blade about the longitudinal axis in a second direction opposed to the first direction.

In some embodiments the cutting section comprises a rotator housed within a case defining one or more slots configured to receive the at least one blade.

In some embodiments each blade extends radially from the rotator and wraps concentrically about an inside surface of the case in the collapsed position.

In some embodiments each blade is expandable and retractable within the slot.

In some embodiments each blade extends radially from the rotator through the slot in the expanded position.

In some embodiments the cutting section is configured to incise the mitral valve leaflet with a predetermined pattern.

In some embodiments the predetermined pattern is selected from the group consisting of: a T-shaped incision, a linear incision, and an X-shaped incision.

In some embodiments the at least one blade extends radially away from a longitudinal axis defined by the apparatus and in a configuration that corresponds to the predetermined pattern.

In some embodiments the controller is configured to move the cutting section from the collapsed position to the expanded position and vice versa.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 4A is a top elevation view of an apparatus for use in replacing a mitral valve in a collapsed position according to an example embodiment of the present invention.

FIG. 4B is a side elevation view of the apparatus shown in FIG. 4A in the collapsed position.

FIG. 4C is a top elevation view of the apparatus shown in FIG. 4A in an expanded position.

FIG. 4D is a side elevation view of the apparatus shown in FIG. 4A in the expanded position.

FIG. 4E is a rear, side perspective view of the apparatus shown in FIG. 4A in the expanded position.

FIG. 4F is an exploded view of the apparatus show in FIG. 4A in the expanded position.

FIG. 6A is a schematic illustration of a mitral valve anterior leaflet incised with an apparatus for use in replacing a mitral valve in according to an example embodiment of the present invention.

FIG. 6B is a schematic illustration of a mitral valve anterior leaflet incised with an apparatus for use in replacing a mitral valve in according to an example embodiment of the present invention.

FIG. 6C is a schematic illustration of a mitral valve anterior leaflet incised with an apparatus for use in replacing a mitral valve in according to an example embodiment of the present invention.

FIG. 6D is a schematic illustration of a mitral valve anterior leaflet incised with an apparatus for use in replacing a mitral valve in according to an example embodiment of the present invention.

FIG. 6E is a schematic illustration of a mitral valve anterior leaflet incised with an apparatus for use in replacing a mitral valve in according to an example embodiment of the present invention.

FIG. 9C is a partial top elevation view of the apparatus shown in FIG. 9A in the collapsed position.

FIG. 9D is a front elevation view of the apparatus shown in FIG. 9A in the collapsed position.

FIG. 10O is a front elevation cross-sectional view of the apparatus show in FIG. 10A in an expanded position.

FIG. 10D is a partial side elevation view of the apparatus shown in FIG. 10A in the expanded position.

FIG. 12A is a schematic illustration of a subject's body having an apparatus for use in replacing a mitral valve according to an example embodiment of the present invention inserted intravascularly, wherein a snare is advanced through a first catheter into a left atrium of the subject's heart and a guidewire of the apparatus is advanced through a second catheter to a left ventricle of the subject's heart.

FIG. 12B is a schematic illustration of the subject's body, heart, and apparatus shown in FIG. 12A, wherein the guidewire of the apparatus is advanced through an anterior mitral valve leaflet into the left atrium of the heart to engage the snare.

FIG. 12C is a schematic illustration of the subject's body, heart, and apparatus shown in FIG. 12A, wherein a cutter of the apparatus is advanced in the second catheter to the left ventricle of the heart and a transcatheter heart valve prosthesis is advanced over a guidewire of the apparatus to a position in the left atrium above the anterior leaflet of the mitral valve.

FIG. 12D is a schematic illustration of the subject's body, heart, and apparatus shown in FIG. 12C, wherein the cutter of the apparatus is advanced from the second catheter to a ventricular surface of the anterior mitral valve leaflet of the heart.

FIG. 12E is a schematic illustration of the subject's body, heart, and apparatus shown in FIG. 12C, wherein the cutter of the apparatus is expanded in the left ventricle of the heart.

FIG. 12F is a schematic illustration of a cross-section of a punctured mitral valve leaflet shown in FIG. 12E taken along the line B-B.

FIG. 12G is a schematic illustration of the subject's body, heart, and apparatus shown in FIG. 12C, wherein the cutter of the apparatus is advanced in an expanded position through the anterior mitral valve leaflet of the heart.

FIG. 12H is a schematic illustration of a cross-section of an incised mitral valve leaflet shown in FIG. 12G taken along the line A-A.

DESCRIPTION

Figure 1:
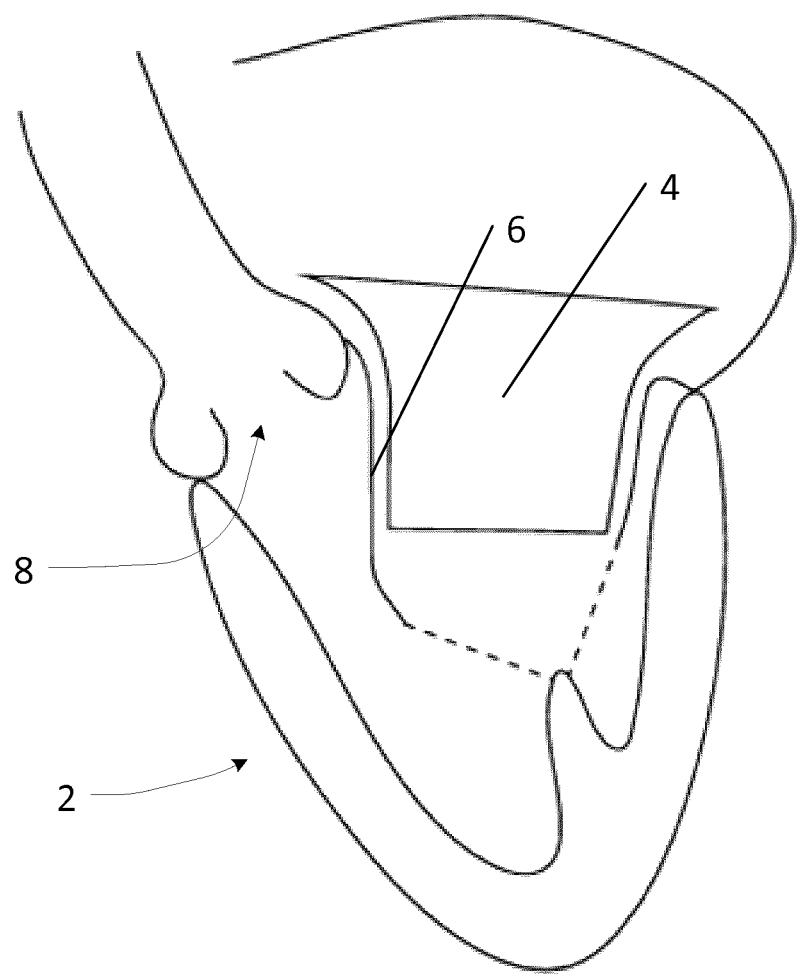
FIG. 1 is a side elevation cross-sectional view of a heart showing LVOT obstruction by a mitral valve prosthesis.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless context dictates otherwise, the term "anterior" (as used herein in relation to a subject's body and parts thereof) refers to a position that is more near the front surface of the subject's body or part thereof than the rear surface of the subject's body or part thereof.

Unless context dictates otherwise, the term "posterior" (as used herein in relation to a subject's body and parts thereof) refers to a position that is more near the rear surface of the subject's body or part thereof than the front surface of the subject's body or part thereof.

Unless context dictates otherwise, the term "proximal" (as used herein in relation to an apparatus according to an example embodiment of the present invention and parts thereof) refers to a position that is more near a controller of the apparatus or part thereof.

Unless context dictates otherwise, the term "distal" (as used herein in relation to an apparatus according to an example embodiment of the present invention and parts thereof) refers to a position that is situated further away from a controller of the apparatus or part thereof.

Unless context dictates otherwise, the terms "percutaneous", "percutaneously", and the like (as used herein) refer to a method of accessing a subject's circulatory system and/or heart through the skin, such as by needle access.

Unless context dictates otherwise, the term "antegrade" (as used herein) refers to a percutaneous approach to a mitral valve via a subject's femoral vein, right atrium, atrial septal puncture, and left atrium.

Unless context dictates otherwise, the term "retrograde" (as used herein) refers to a percutaneous approach to a mitral valve via a subject's femoral artery, wherein the left ventricle is accessed via the aortic valve.

Unless context dictates otherwise, the term "intravascular" (as used herein) means situated or occurring within a subject's blood vessel or circulatory system.

Unless context dictates otherwise, the term "external" (as used herein in relation to a subject's body and parts thereof) means situated outside of a subject's circulatory system or body.

Unless context dictates otherwise, the term "transcatheter" (as used herein) refers to a method performed intravascularly through the lumen of a catheter.

Unless context dictates otherwise, the term "collapsed position" (as used herein) refers to a radially compressed state. Although the terms "radial", "radially", and the like are most commonly used in connection with circular objects or features, it should be understood for the purpose of this description and accompanying aspects that the terms "radial", "radially", and the like are used in a broader context and are not limited to describing strictly circular objects or features or objects or features with strictly circular cross-section.

Unless context dictates otherwise, the term "expanded position" (as used herein) refers to a radially enlarged, extended, or otherwise broadened state.

Unless context dictates otherwise, the term "circulatory system" (as used herein) refers to a system that circulates blood and/or lymph through a subject's body, consisting of one or more of a heart, blood vessels, blood, lymph, lymphatic vessels, and lymphatic glands.

Unless context dictates otherwise, the term "transcatheter heart valve prosthesis" (as used herein) refers to a prosthesis used to repair or replace a heart valve (e.g. mitral valve, aortic valve, etc.) percutaneously using a transcatheter heart valve delivery system, including (but not limited to) a transcatheter mitral valve prosthesis.

Unless the context dictates otherwise, "subject" (as used herein) refers to a human and/or an animal (i.e. a bird and/or a mammal) and includes any subject that will benefit or that is likely to benefit from the present invention (for example, a subject with a condition affecting the normal functioning of a heart valve, including (but not limited to) the mitral valve, for example, mitral valve regurgitation, mitral valve prolapse, and mitral valve stenosis.

Unless the context dictates otherwise, "nitinol" (as used herein) refers to a nickel-titanium alloy with shape memory and/or superelastic characteristics. Nitinol is capable of deforming into a deformed shape and recovering its original, undeformed shape without applying heat.

Although the methods and apparatus of the present invention may be used for the percutaneous repair of any of the cardiac valves, the following description will focus on the replacement of mitral valves. Further, while the methods and apparatus of the present invention will preferably be percutaneous and intravascular, such methods and apparatus may be used for performing open heart surgery where the heart is accessed through the myocardial tissue and/or in minimally invasive procedures where access to the heart is achieved thorascopically. Further still, while the methods and apparatus of the present invention will preferably be used with conventional transcatheter heart valve prostheses, such methods and apparatus may be used with prostheses implanted through the myocardial tissue of the heart and/or prostheses implanted using minimally invasive procedures where access to the heart is achieved thorascopically.

Figure 2A:
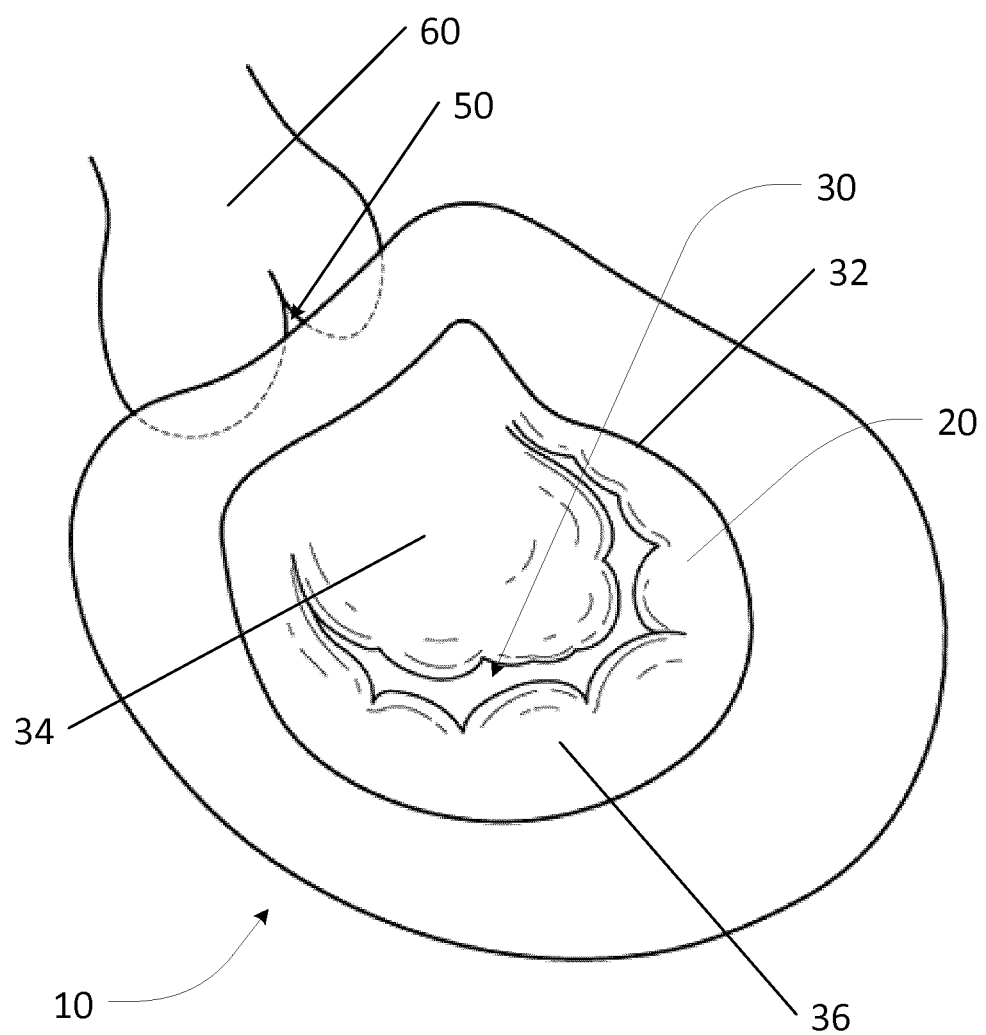
FIG. 2A is a top cross-sectional view of a heart showing normal coaptation of the mitral valve.
Figure 2B:
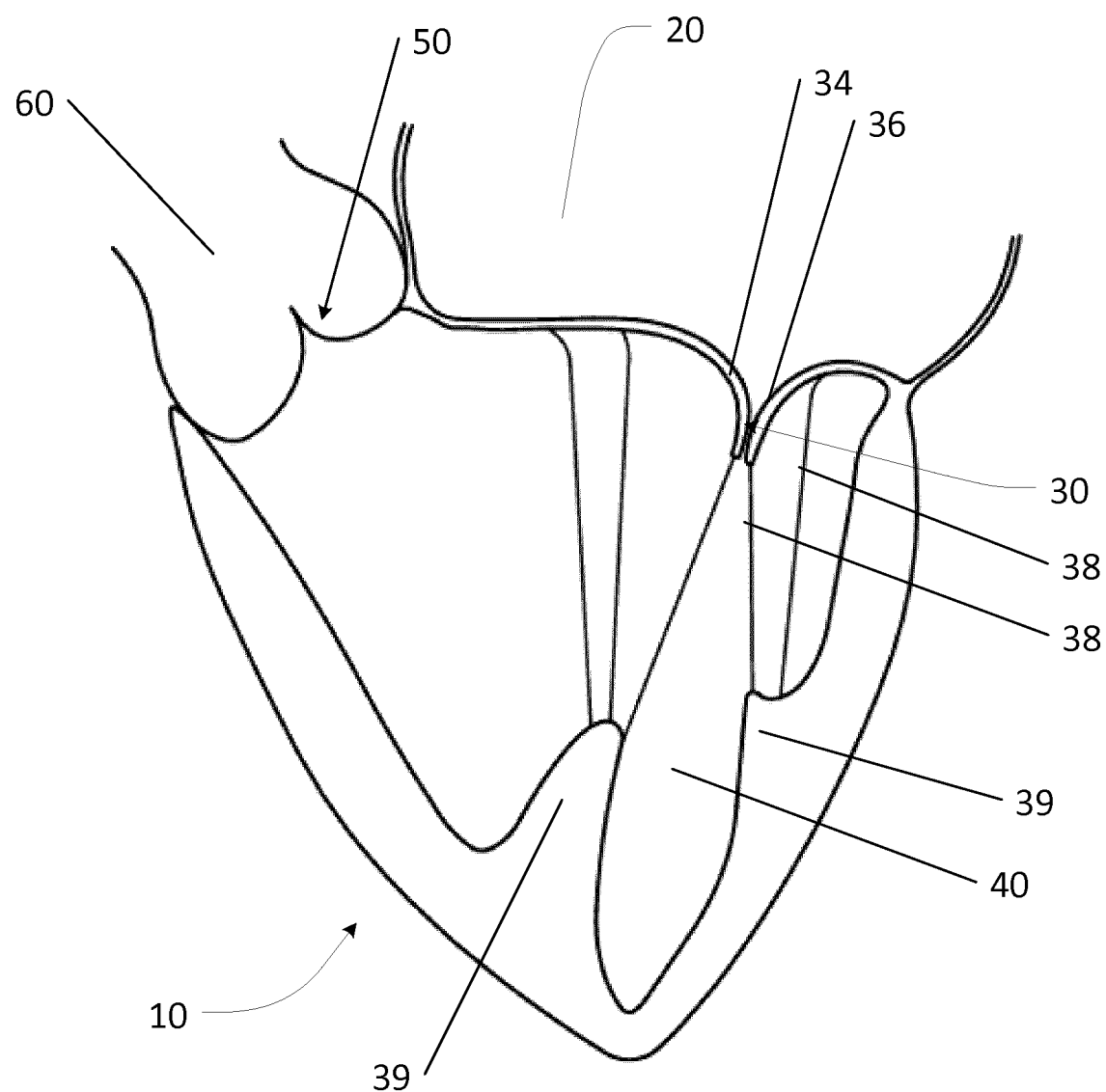
FIG. 2B is a side elevation cross-sectional view of the heart shown in FIG. 2A.

The human heart 10, shown in FIGS. 2A and 2B, is a muscle pump which relies on heart valves to achieve forward blood flow. In normal physiology, oxygenated blood returning from the lungs is collected in a left atrium 20, and then passes through a mitral (inlet) valve 30 to enter a left ventricle 40 (i.e. the pumping chamber). With contraction of left ventricle 40, the elevation of left ventricular pressure causes mitral valve 30 to close, preventing reversal of blood flow back into atrium 20. As ventricular pressure exceeds aortic pressure, aortic (outlet) valve 50 opens, and blood is pumped forward into aorta 60. When left ventricle 40 relaxes, the ventricular pressure drops, mitral valve 30 reopens to permit flow of blood from left atrium 20 to left ventricle 40, and the process repeats.

Mitral valve 30 separates left atrium 20 from left ventricle 40, and is comprised of a mitral annulus 32, leaflets (anterior 34 and posterior 36), chordae tendinae 38, and papillary muscles 39. During ventricular contraction (systole), the ventricular pressure rises, which forces displacement of mitral valve leaflets 34, 36 towards atrium 20 (i.e. commonly known as atrial or leaflet displacement). The length and integrity of chordae tendinae 38 determines the degree of leaflet displacement. In normal physiology, equal displacement of anterior mitral valve leaflet 34 and posterior mitral valve leaflet 36 results in contact (coaptation) between the leaflets, and consequent competence of mitral valve 30.

Figure 3:
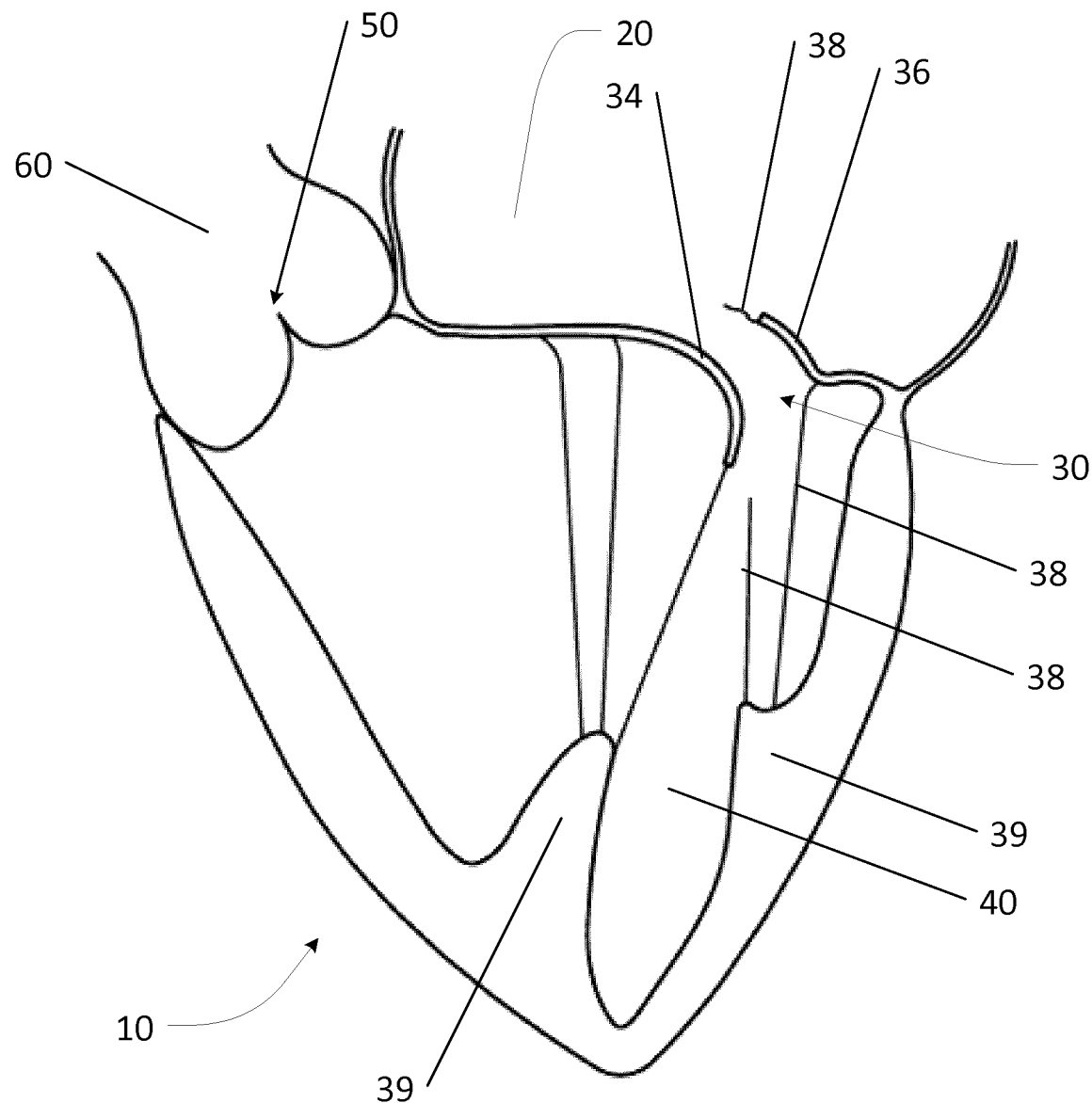
FIG. 3 is a side elevation cross-sectional view of a heart showing prolapse of a posterior mitral valve leaflet.

In circumstances where mitral valve leaflet 34 and/or 36 is supported by chordae tendinae 38 which are elongated or ruptured, ventricular contraction may result in excessive atrial displacement of the leaflet(s), and this may prevent coaptation between the leaflets (FIG. 3). This is referred to as mitral valve leaflet prolapse. In this circumstance, the competency of mitral valve 30 may be compromised and leakage may occur. Leakage through the mitral valve is referred to as mitral regurgitation, and when it is due to mitral valve leaflet prolapse it is referred to as degenerative mitral regurgitation. In other circumstances, the ventricular muscle itself can be diseased and its function impaired causing limited ventricular contraction and progressive ventricular dilation. Since mitral valve leaflets 34, 36 are attached by chordae tendinae 38 to the ventricular muscle, ventricular dilation can limit leaflet movement toward atrium 20 during contraction, resulting in poor leaflet coaptation and causing mitral regurgitation. This is referred to as functional mitral regurgitations.

The methods and apparatus of example embodiments of the present invention use existing transcatheter heart valve prostheses to percutaneously replace a mitral valve. The methods and apparatus of example embodiments of the present invention are used to percutaneously incise an anterior mitral valve leaflet and to permit precise implantation of a transcatheter heart valve prosthesis in that incision. In this way, incision and implantation are both controlled, deliberate, and precise and LVOT obstruction may be avoided or minimized.

In some embodiments the size and design of the incision may be controlled to optimize implantation. Some embodiments of the present invention use percutaneous incision of the anterior mitral valve leaflet to allow a transcatheter heart valve prosthesis to be implanted after the mitral valve leaflet is incised to reduce or eliminate the risk of hemodynamic instability.

Figure 5:
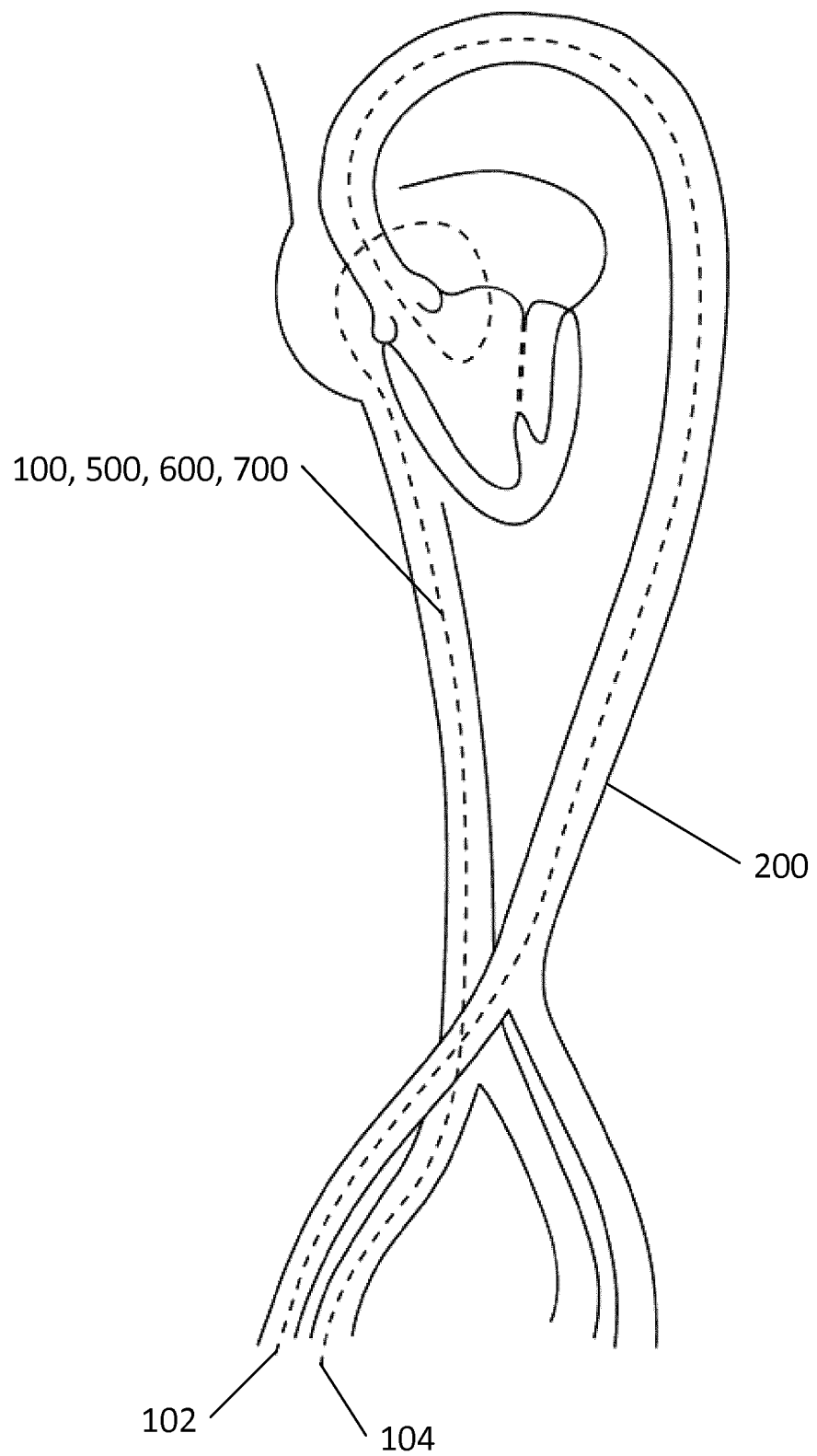
FIG. 5 is a schematic illustration of an apparatus for use in replacing a mitral valve intravenously traversing a subject's circulatory system according to an example embodiment of the present invention.

An apparatus 100 for use in replacing a heart valve, such as a mitral valve, is shown in FIGS. 4A-4F. Alternate embodiments, apparatus 500, apparatus 600, and apparatus 700, are shown in FIGS. 8A-8J, 9A-9H, and 10A-10D. Many features and components of apparatus 500, 600, 700 are similar to features and components of apparatus 100, with the same reference numerals being used to indicate features and components that are similar between the embodiments. In some embodiments apparatus 100, 500, 600, 700 is used to percutaneously incise an anterior mitral valve leaflet and to permit precise implantation of a transcatheter heart valve prosthesis in the incision. Apparatus 100, 500, 600, 700 is sized and dimensioned to traverse a subject's circulatory system percutaneously from a first access site to a second access site. In some embodiments the first access site enters the subject's femoral artery or femoral vein. In some embodiments the second access site enters the subject's femoral artery or femoral vein. When the first access site enters the subject's femoral artery, the second access site enters the subject's femoral vein and vice versa. The example embodiment of apparatus 100 shown in FIGS. 5 and 11A-11J traverses a subject's circulatory system 200 from a first access site 106 (FIGS. 11A-11J) to a second access site 108 (FIGS. 11A-11J) such that proximal end 102 and distal end 104 of apparatus 100 are external to the subject's body when apparatus 100 is situated intravascularly and traverses a subject's circulatory system. Apparatus 500, 600, 700 are similarly situated in a subject's circulatory system. In the embodiment illustrated in FIG. 5, proximal end 102 is external the femoral artery and distal end 104 is external the femoral vein when apparatus 100 is situated intravascularly and traverses the subject's circulatory system. However, this is not necessary and the proximal end 102 may be external the femoral artery and the distal end 104 may be external the femoral vein when apparatus 100 is situated intravascularly and traverses the subject's circulatory system.

The apparatus includes a controller, a cutting section, and a guidewire. The apparatus is configured to be operated external to a subject's body. For example, the controller may be operated external to the subject's body to advance the apparatus intravascularly through the subject's circulatory system from a first access site (e.g. access site 106 (FIGS. 11A-11J)) to a second access site (e.g. access site 108 (FIGS. 11A-11J)). In some embodiments the controller is configured to operate the cutting section and/or the guidewire intravascularly from outside the subject's body, as described elsewhere herein.

The controller (e.g. controller 110) is operable to move the apparatus between a collapsed position and an expanded position. In the collapsed position, the apparatus is in a radially compressed state to intravascularly traverse a subject's circulatory system. In the expanded position, the apparatus is in a radially enlarged, extended, or otherwise broadened state whereby the radial cross-sectional area of the apparatus is greater in the expanded position than in the collapsed position. In the expanded position, the apparatus is operable for incising a mitral valve leaflet. In some embodiments the cutting section (e.g. cutting section 120, 520, 620, 720) is operable to move the apparatus between a collapsed position (FIGS. 4A, 4B, 8A-8D, 8I, 9A-9D and 10A-10B) and an expanded position (FIGS. 4C-4F, 8E-8H, 8J, 9E-9H, and 10C-10D). In the collapsed position, the cutting section is in a radially compressed state to reduce the cross-sectional area of the cutting section. In the expanded position, the cutting section is in a radially enlarged, extended, or otherwise broadened state whereby the radial cross-sectional area of the cutting section is greater in the expanded position than in the collapsed position.

A guidewire (e.g. guidewire 130, 530, 630, 730) longitudinally extends from the cutting section for guiding and positioning the cutting section to incise a mitral valve leaflet and for positioning a transcatheter heart valve prosthesis (e.g. a mitral valve prosthesis) into the incised leaflet as described elsewhere herein. In this way, the transcatheter heart valve prosthesis may be precisely positioned within the incision following incision to reduce or eliminate the risk of hemodynamic instability. In some embodiments the transcatheter heart valve prosthesis is positioned within the incision within less than about 5 seconds following incision. In some embodiments the transcatheter heart valve prosthesis is positioned within the incision within less than about 3 seconds following incision. In some embodiments the transcatheter heart valve prosthesis is positioned within the incision within less than about 1 second following incision. In some embodiments the transcatheter heart valve prosthesis is closely or immediately positioned within the incision following incision. Precise positioning of the transcatheter heart valve prosthesis may avoid or minimize LVOT obstruction. Immediate positioning of the transcatheter heart valve prosthesis following incision may minimize the risk of hemodynamic instability.

In the embodiment illustrated in FIGS. 4A-4F, apparatus 100 includes a cutting section 120, a guidewire 130 extending away from a distal end of cutting section 120, and a controller 110 extending away from a proximal end of cutting section 120 opposed to the distal end. In the embodiment illustrated in FIGS. 4A-4F, controller 110 includes a handle 116 and a knob 118. Handle 116 has a lumen (not shown) extending longitudinally therethrough. A rod 119 coupled to knob 118 extends through the lumen and slides within the lumen to move rod 119 and knob 118 concentrically and/or longitudinally relative to handle 116. By longitudinally sliding and/or rotating knob 118 relative to handle 116, apparatus 100 may be operated. In some embodiments cutting section 120 is rotatable relative to controller 110. In some other embodiments, controller 110 and cutting section 120 are rotatably fixed such that rotation of controller 110 rotates cutting section 120.

Guidewire 130 comprises a proximal end 132 (FIG. 4F) coupled to cutting section 120 and a distal end 134 opposed to the proximal end. In some embodiments guidewire 130 is rotatable relative to controller 110 and/or cutting section 120. In some other embodiments, cutting section 120 and guidewire 130 are rotatably fixed such that rotation of cutting section 120 rotates guidewire 130 and vice versa. In the illustrated embodiment, distal end 134 of guidewire 130 includes a hook 136 for engaging a snaring guidewire as described elsewhere herein. Other means for engaging a snaring guidewire are considered to be within the knowledge of persons skilled in the art of interventional cardiology.

Cutting section 120 includes one or more radially expandable blades 126 for incising a mitral valve leaflet. Each blade 126 may be expanded or contracted using controller 110. In the embodiment illustrated in FIGS. 4A-4F, cutting section 120 includes three radially expandable blades 126 configured to incise the mitral valve leaflet with a "T-shaped" incision. The number and configuration of the blades of apparatus 100 may be selected to achieve other desired incision patterns. For example, the number and configuration of blades 126 may be selected to incise a mitral valve leaflet with a "T-shaped" incision, a linear incision, or an "X-shaped" incision (FIGS. 6A-6E). Other incision patterns are considered to be within the knowledge of persons skilled in the art of heart surgery. In some embodiments, each blade 126 is expandable and retractable within a corresponding blade window (not shown) defined by the cutting section.

In the embodiment illustrated in FIGS. 4A-4F, each blade 126 comprises a cutting blade 126a pivotally coupled to a lever arm 126b by a hinge 126c. Hinge 126c may comprise a pin, a screw, or another mechanical fastener conventionally known. To expand and collapse blades 126, cutting section 120 includes a rod 129 coupled to rod 119 at a proximal end 129a and coupled to lever arm 126b at a distal end 129b (FIG. 4F). In some embodiments rods 119, 129 are coupled together. In some other embodiments, rods 119, 129 are formed together as a unitary rod (not shown). In some embodiments lever arm 126b is pivotally coupled to distal end 129b by a hinge (not shown), such as a pin, a screw, or another mechanical fastener conventionally known. Cutting blade 126a is coupled to a proximal end 132 of guidewire 130. In some embodiments cutting blade 126a is pivotally coupled to guidewire 130 by a hinge (not shown), such as a pin, a screw, or another mechanical fastener conventionally known.

In a collapsed position (FIGS. 4A-4B), cutting blade 126a and lever arm 126b are folded together about hinge 126c in a radially compressed state to reduce the cross-sectional area of cutting section 120 so that apparatus 100 may be inserted percutaneously and traversed intravascularly. To expand cutting section 120 (FIGS. 4C-4F), knob 118 coupled to rod 119 is pulled away from handle 116 along an axis A defined by apparatus 100 (FIG. 4A). In this way, rod 129 coupled to rod 119 longitudinally slides within the lumen (not shown) defined by handle 116, thereby pulling distal end 129b of rod 129 away from proximal end 132 of guidewire 130. As distal end 129b is pulled away from guidewire 130 along axis A, cutting blade 126a and lever arm 126b unfold about hinge 126c and radially extend away from axis A. In this way, cutting blade 126a is oriented to incise a mitral valve leaflet as described elsewhere herein. To collapse cutting section 120, knob 118 is pushed toward handle 116 along axis A, drawing distal end 129b of rod 129 toward proximal end 132 of guidewire 130 and folding cutting blade 126a and lever arm 126b about hinge 126c. Cutting blade 126a and lever arm 126b radially compress towards axis A. In the collapsed position, apparatus 100 may be inserted into a catheter (e.g. catheter 12).

In the illustrated embodiment, apparatus 100 includes a blade tube 121 (although this is not necessary). Blade tube 121 defines a lumen (not shown) extending longitudinally therethrough and one or more slots 121c, each slot 1221c configured to permit blade 126 to pass therethrough. Distal end 129b of rod 129 and proximal end 132 of guidewire 130 extend through the lumen. In this way blade tube 121 spans a gap between distal end 129b of rod 129 and proximal end 132 of guidewire 130 when apparatus 100 is in an expanded position. Accordingly, blade tube 121 couples cutting section 120 and guidewire 130 together along axis A. Blade tube 121 prevents material from becoming lodged between cutting section 120 and guidewire 130 when apparatus 100 is in an expanded position. Blade tube 121 may enhance the precision of apparatus 100 in incising a mitral valve leaflet and implanting a transcatheter heart valve prosthesis as described elsewhere herein.

In the illustrated embodiment, apparatus 100 includes a connecting tube 123 (although this is not necessary). Connecting tube 123 defines a lumen (not shown) extending longitudinally therethrough. A distal end 121b of blade tube 121 and proximal end 132 of guidewire 130 extend through the lumen. In this way connecting tube 123 rigidly couples cutting section 120 and guidewire 130 together along axis A. Connecting tube 123 may enhance the precision of apparatus 100 in incising a mitral valve leaflet and implanting a transcatheter heart valve prosthesis as described elsewhere herein.

In the illustrated embodiment, apparatus 100 includes a rod tube 125 (although this is not necessary). Rod tube 125 defines a lumen (not shown) extending longitudinally therethrough. A proximal end 121a of blade tube 121 and rod 129 extend through the lumen and longitudinally slides within the lumen. Rod tube 125 may enhance the rigidity of apparatus 100. For example, rod tube 125 may rigidly couple controller 110 and cutting section 120 together along axis A. Rod 119 and/or rod 129 are slidable within the lumen of rod tube 125 along axis A.

In the illustrated embodiment, apparatus 100 includes a tube 127 (although this is not necessary). Tube 127 defines a lumen (not shown) extending longitudinally therethrough. A proximal end 121a of blade tube 121 and rod tube 125 (and/or rod 129) extend through the lumen and longitudinally slides within the lumen. Tube 127 may enhance the rigidity of apparatus 100.

In some embodiments apparatus 100 and/or the parts thereof comprise a sterilized or sterilisable material. In some embodiments, apparatus 100 and/or the parts thereof comprise one or more of medical grade plastic, thermal plastic, stainless steel, metal, a metal alloy (e.g. nitinol or another nickel/titanium alloy), and titanium. Persons skilled in the art will recognize that apparatus 100 and/or the parts thereof may be made of any sterilized or sterilisable material conventionally used to manufacture tools used in heart surgery.

Figure 7:
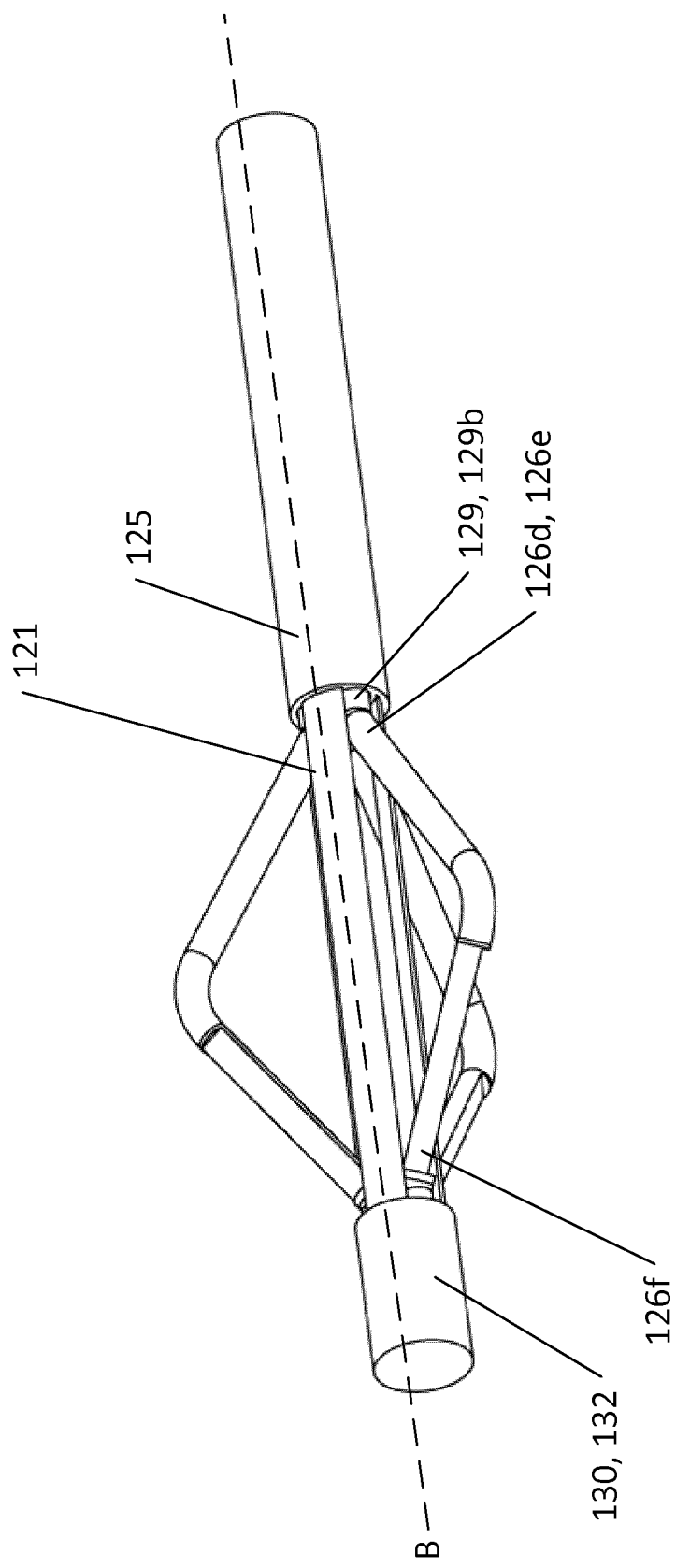
FIG. 7 is a partial perspective view of the apparatus shown in FIG. 4A, wherein the blades are formed from a memory material and are in a pre-deformed state.

In some embodiments, each blade 126 is formed from a sterilized or sterilisable memory material, such as a memory metal alloy including (but not limited to) stainless steel and/or nickel and/or titanium and/or nitinol. For example, blades 126d shown in FIG. 7 are constructed in one-piece from a sterilized or sterilisable memory material, such as a memory metal alloy including (but not limited to) stainless steel and/or nickel and/or titanium and/or nitinol. Blade 126d retains a pre-deformed shape in the expanded position shown in FIG. 7. Each blade 126d is deformable into the collapsed position (not shown).

To expand and collapse blade 126d, a proximal end 126e of blade 126d is coupled to distal end 129b (FIG. 4F) of rod 129. In some embodiments proximal end 126e is pivotally coupled to rod 129 by a hinge (not shown), such as a pin, a screw, or another mechanical fastener conventionally known. A distal end 126f of blade 126d is coupled to a proximal end 132 of guidewire 130. In some embodiments distal end 126f is pivotally coupled to guidewire 130 by a hinge (not shown), such as a pin, a screw, or another mechanical fastener conventionally known.

In a collapsed position (not shown), blade 126d is deformed in a radially compressed state to reduce the cross-sectional area of cutting section 120 so that apparatus 100 may be inserted percutaneously and traversed intravascularly. To expand cutting section 120, knob 118 coupled to rod 119 is advanced toward handle 116 along an axis B defined by apparatus 100 (FIG. 7). In this way, rod 129 coupled to rod 119 longitudinally slides within the lumen (not shown) defined by handle 116, thereby pushing distal end 129b of rod 129 toward proximal end 132 of guidewire 130. As distal end 129b is advanced toward guidewire 130 along axis B, the distance between ends 126e, 126f of blade 126d decreases and blade 126d radially expands away from axis B into its pre-deformed state. In this way, blade 126*d* is oriented to incise a mitral valve leaflet as described elsewhere herein. To collapse cutting section 120, knob 118 is pulled away from handle 116 along axis B, drawing distal end 129*b* of rod 129 away from proximal end 132 of guidewire 130. As distal end 129*b* is pulled away from guidewire 130 along axis B, the distance between ends 126*e*, 126*f* of blade 126*d* increases, which radially collapses blade 126*d* towards axis B into its deformed state. In the collapsed position, apparatus 100 may be inserted into a catheter (e.g. catheter 12).

In the embodiment illustrated in FIGS. 8A-8J, apparatus 500 includes a cutting section 520, a guidewire 530 extending away from a distal end of cutting section 520, and a controller (not shown) extending away from a proximal end of cutting section 520 opposed to the distal end. Many features and components of the controller are similar to features and components of controller 110 described elsewhere herein. In some embodiments the controller includes a handle (not shown) and a knob (not shown). The handle has a lumen (not shown) extending longitudinally therethrough. A rod (not shown) coupled to the knob extends through the lumen and longitudinally slides within the lumen to move the rod and the knob concentrically and/or longitudinally relative to the handle. By longitudinally sliding and/or rotating the knob relative to the handle, apparatus 500 may be operated.

Cutting section 520 includes one or more radially expandable blades 526 for incising a mitral valve leaflet. Each blade 526 may be expanded or contracted using the controller. In the embodiment illustrated in FIGS. 8A-8J, cutting section 520 includes three radially expandable blades 526 configured to incise the mitral valve leaflet with a "T-shaped" incision. The number and configuration of the blades of apparatus 500 may be selected to achieve other desired incision patterns as described elsewhere herein. Each blade 526 is constructed in one-piece from a sterilized or sterilisable memory material, such as a memory metal alloy including (but not limited to) stainless steel and/or nickel and/or titanium and/or nitinol. Each bade 526 retains a pre-deformed shape in the expanded position shown in FIGS. 8E-8H and 8J. Each blade 526 is deformable into the collapsed position shown in FIGS. 8A-8D and 8I. In some other embodiments (not shown) each blade 526 may comprise a cutting blade pivotally coupled to a lever arm by a hinge. Such blades are structurally and functionally similar to blades 126 of apparatus 100.

To expand and collapse blades 526, cutting section 520 includes a runner 570. A proximal end 526*a* of each blade 526 is coupled to runner 570. A distal end 526*b* of each blade 526 is coupled to guidewire 530. Runner 570 defines a lumen (not shown) extending longitudinally therethrough. Runner 570 is slideably mounted about a rod 528. Rod 528 extends from the controller through the lumen of runner 570 to permit the runner to slide longitudinally across rod 528. Runner 570 is coupled to a distal end 529*a* of a tube 529 for operating cutting section 520. Tube 529 is coupled to handle 116 of the controller for sliding runner 570 along rod 528 by pulling or pushing knob 118. Tube 529 defines a lumen (not shown) extending longitudinally therethrough. Rod 528 extends through the lumen of tube 529.

Figure 8A:
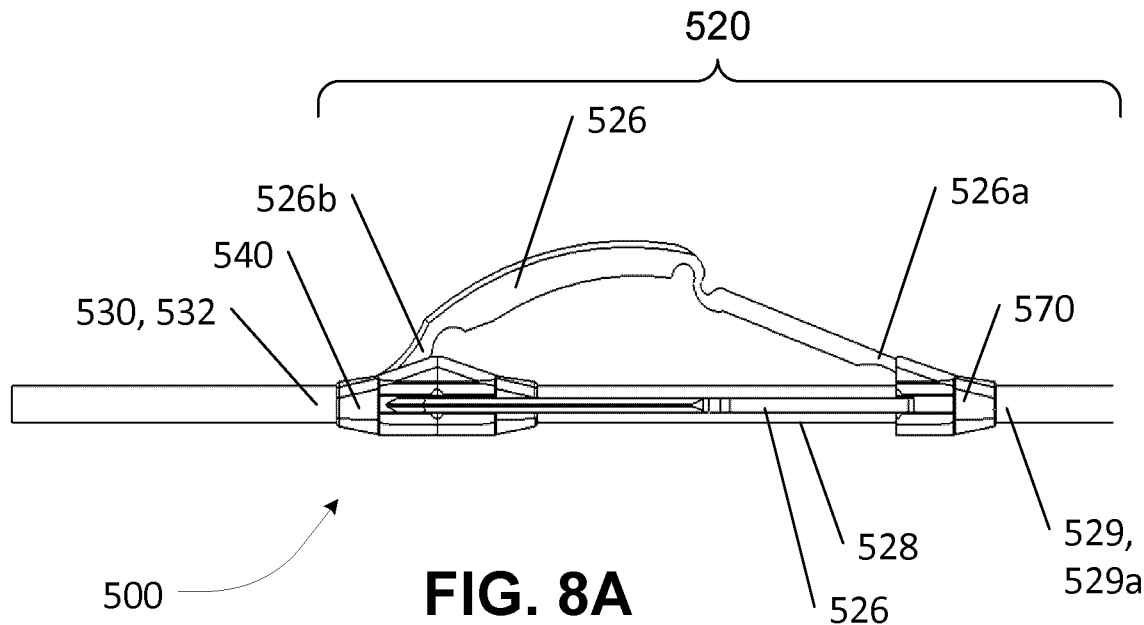
FIG. 8A is a partial side elevation view of an apparatus for use in replacing a mitral valve in a collapsed position according to an example embodiment of the present invention.
Figure 8B:
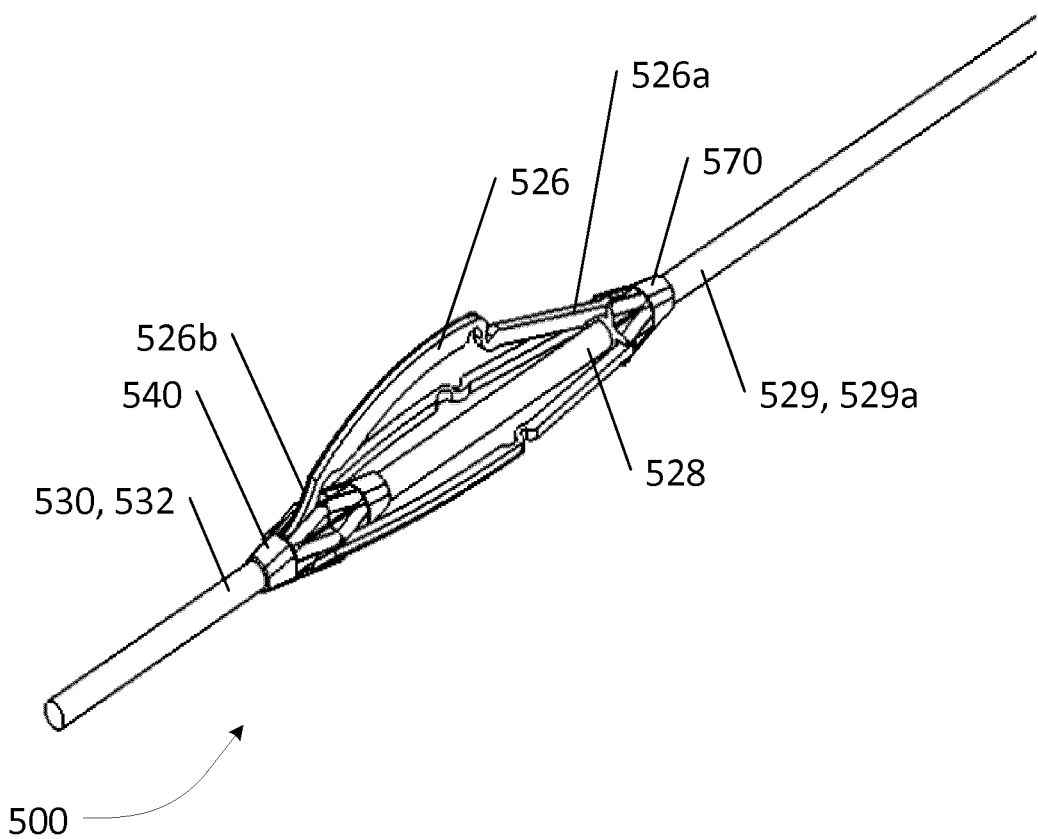
FIG. 8B is a partial front, top, side perspective view of the apparatus shown in FIG. 8A in the collapsed position.
Figure 8D:
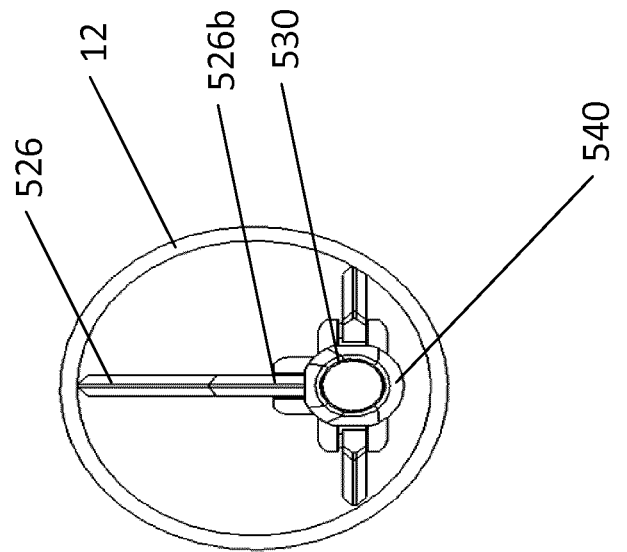
FIG. 8D is a front elevation view of the apparatus shown in FIG. 8A in the collapsed position.
Figure 8C:
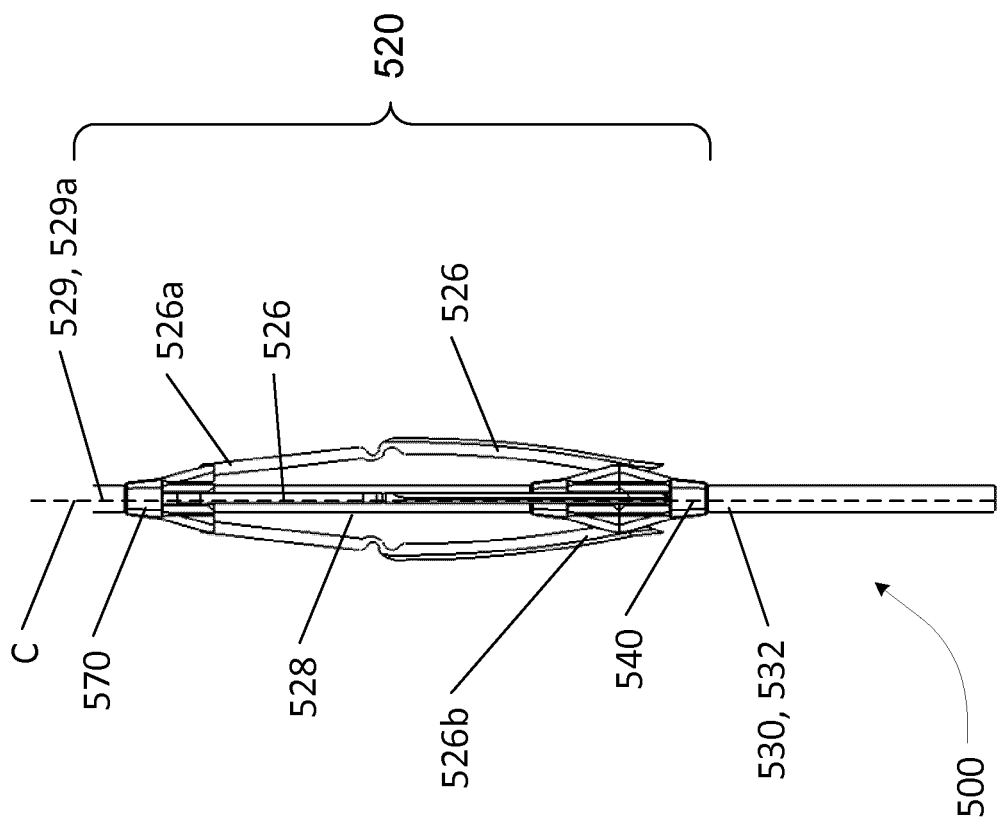
FIG. 8C is a partial top elevation view of the apparatus shown in FIG. 8A in the collapsed position.
Figure 8E:
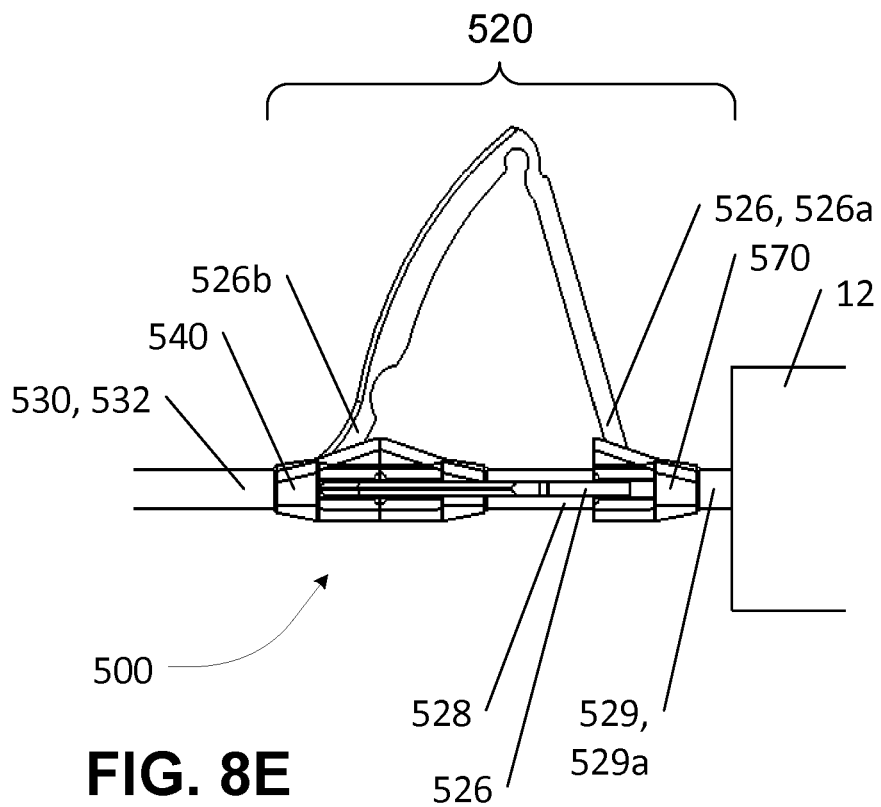
FIG. 8E is a partial side elevation view of the apparatus shown in FIG. 8A in an expanded position.
Figure 8F:
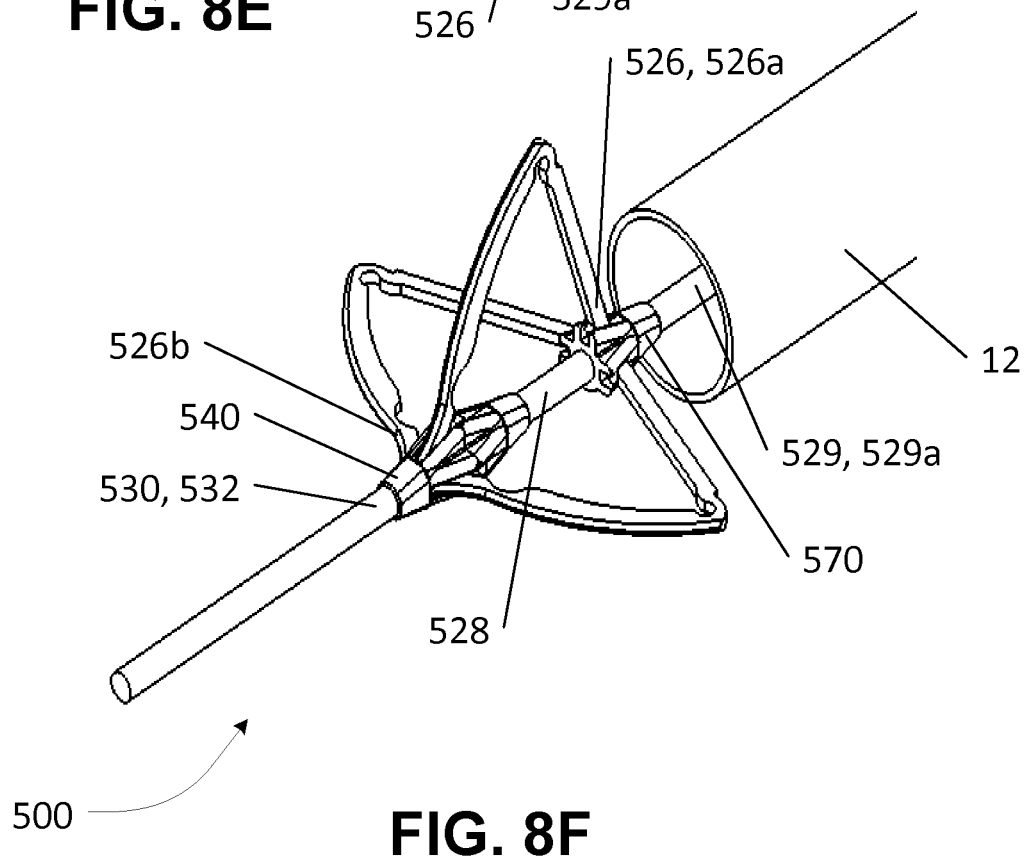
FIG. 8F is a partial front, top, side perspective view of the apparatus shown in FIG. 8A in the expanded position.
Figure 8H:
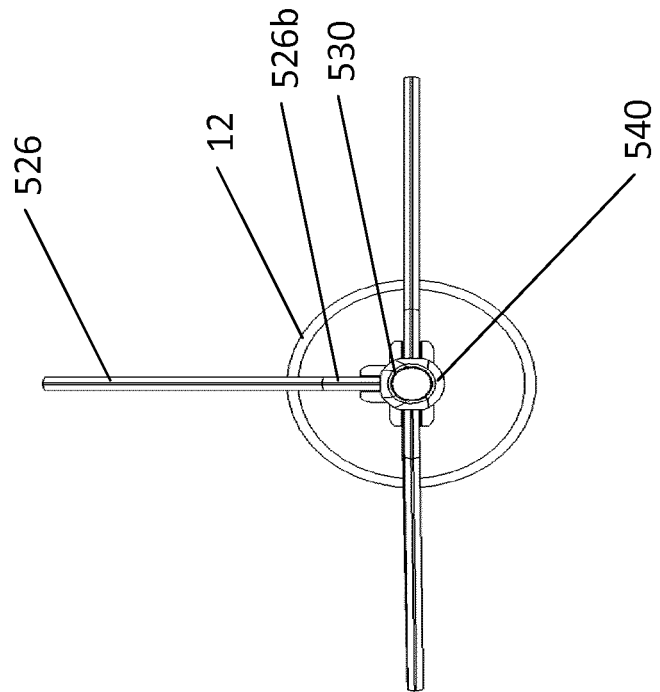
FIG. 8H is a front elevation view of the apparatus shown in FIG. 8A in the expanded position.
Figure 8G:
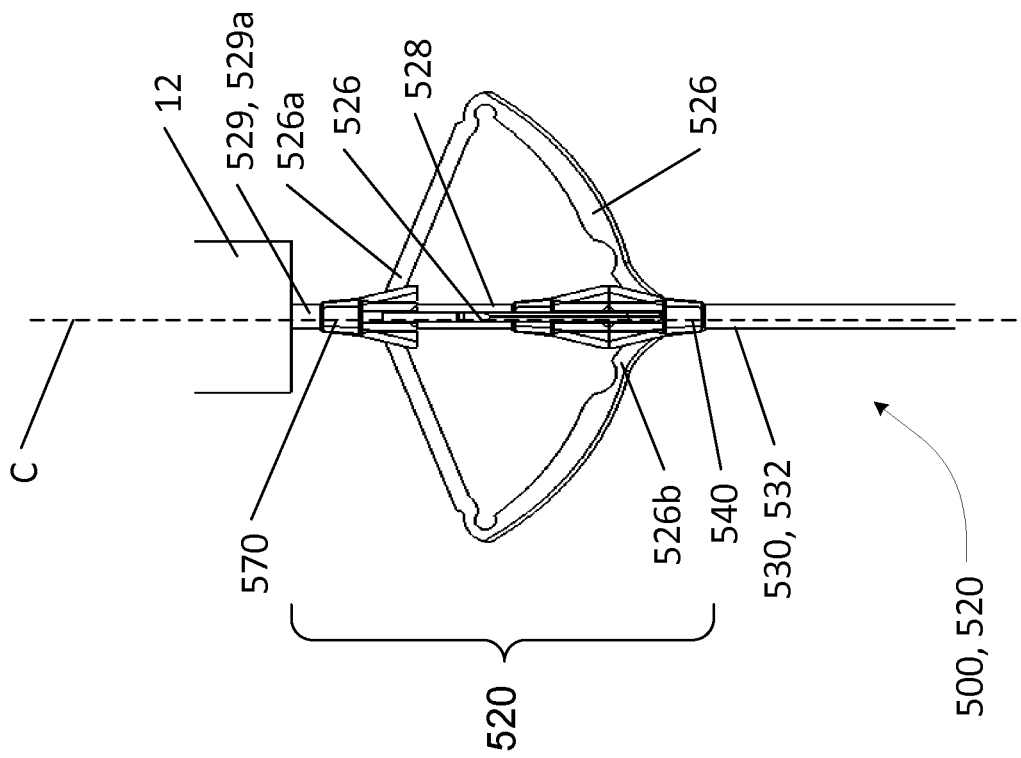
FIG. 8G is a partial top elevation view of the apparatus shown in FIG. 8A in the expanded position.
Figure 8I:
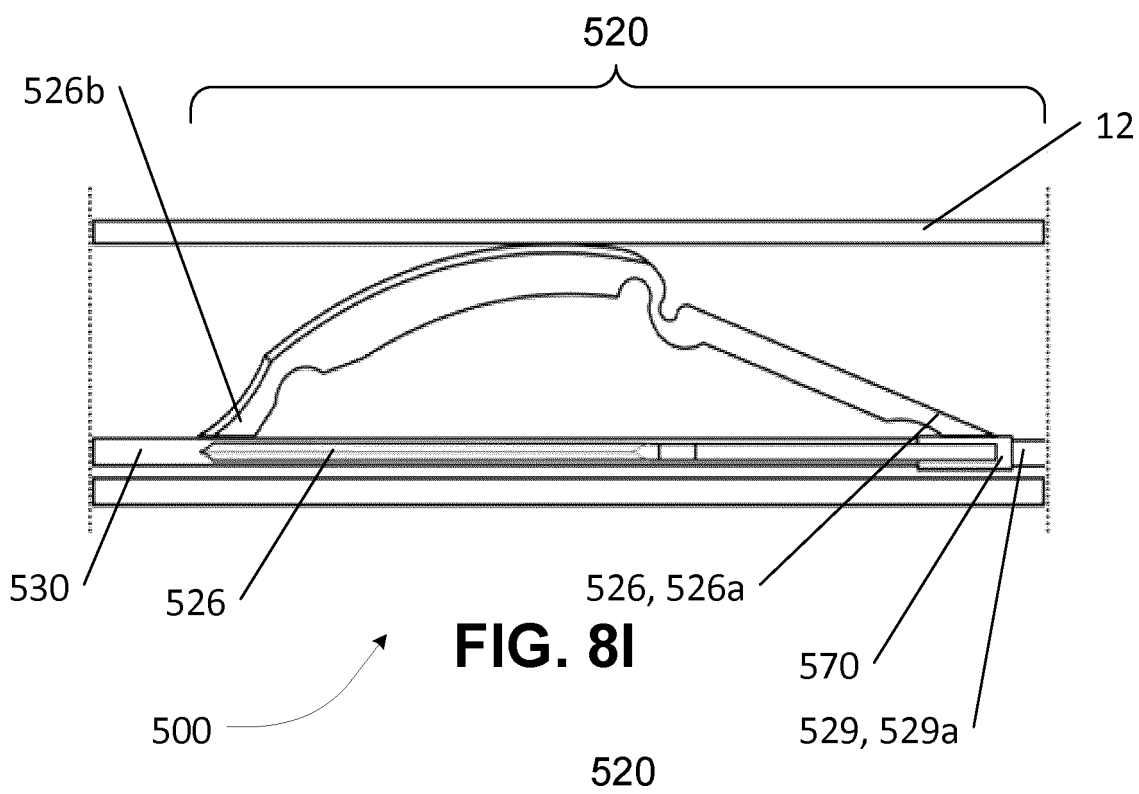
FIG. 8I is a partial side elevation view of the apparatus shown in FIG. 8A in the collapsed position inside a catheter.
Figure 8J:
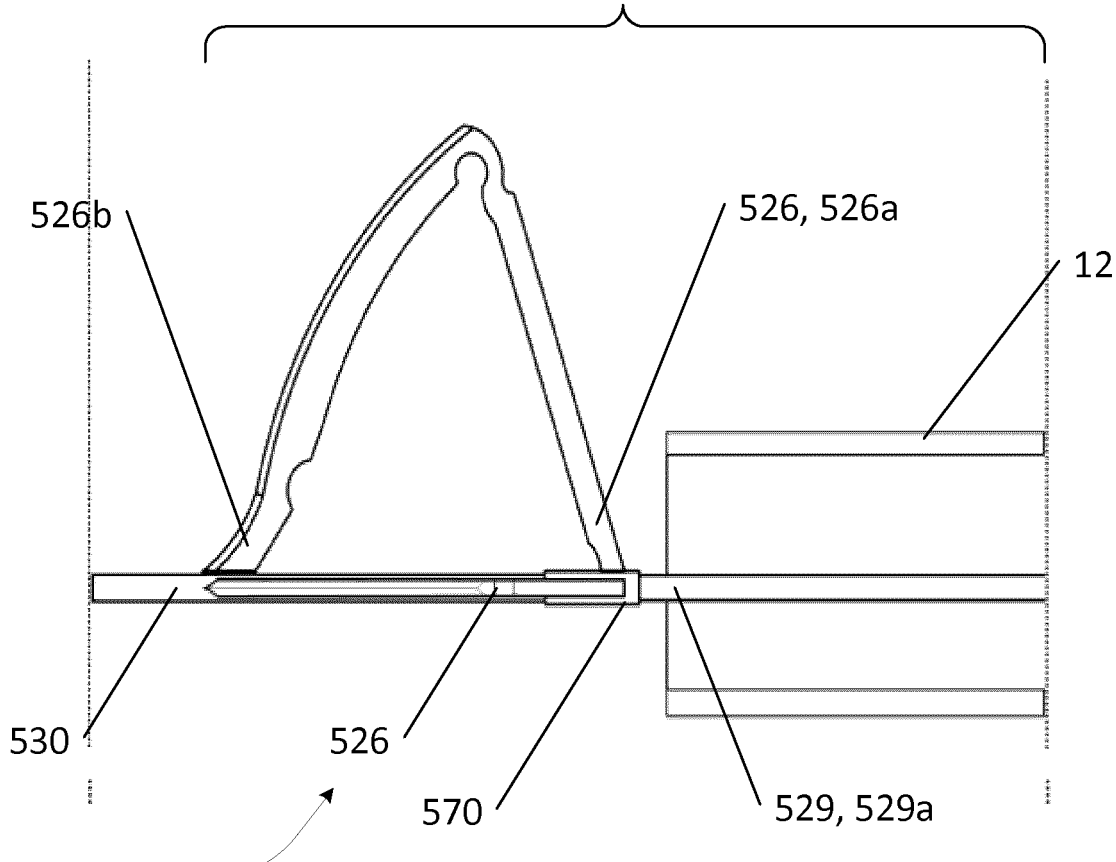
FIG. 8J is a partial side elevation view of the apparatus shown in FIG. 8A withdrawn from the catheter in the expanded position.

In some embodiments, apparatus 500 includes a joint 540 fixedly coupled to a proximal end 532 of guidewire 530 and a distal end 526*b* of each cutting blade 526 is coupled to joint 540. Runner 570 longitudinally slides across rod 528 relative to joint 540. Each blade 526 is movable from a collapsed position (FIGS. 8A-8D and 8I) into a radially expanded position (FIGS. 8E-8H and 8J) by pushing tube 529 toward joint 540 along an axis C defined by apparatus 500 (FIG. 8C). In this way, runner 570 slides along rod 528 towards joint 540. As runner 570 is pushed towards joint 540 along axis C, the distance between ends 526*a*, 526*b* of blade 526 decreases and each blade 526 radially expands away from axis C. In this way, blade 526 is oriented to incise a mitral valve leaflet as described elsewhere herein. To collapse blade 526, tube 529 is pulled away from joint 540 along axis C, drawing runner 570 away from joint 540. As runner 570 is pulled away from joint 540 along axis C, the distance between ends 526*a*, 526*b* of blade 526 increases and each blade 526 radially collapses towards axis C. In the collapsed position, apparatus 500 may be inserted into a catheter (e.g. catheter 12).

In some embodiments apparatus 500 and/or the parts thereof comprise a sterilized or sterilisable material. In some embodiments, apparatus 500 and/or the parts thereof comprise one or more of medical grade plastic, thermal plastic, stainless steel, metal, a metal alloy (e.g. nitinol or another nickel/titanium alloy), and titanium. Persons skilled in the art will recognize that apparatus 500 and/or the parts thereof may be made of any sterilized or sterilisable material conventionally used to manufacture tools used in heart surgery.

In some embodiments, the cutting section includes one or more blades that are rotatably deformable. For example, apparatus 600 shown in FIGS. 9A-9H comprises three rotatably deformable blades 626. In the embodiment illustrated in FIGS. 9A-8H, apparatus 600 includes a cutting section 620, a guidewire 630 extending away from a distal end of cutting section 620, and a controller (not shown) extending away from a proximal end of cutting section 620 opposed to the distal end. Many features and components of the controller are similar to features and components of controller 110 described elsewhere herein. In some embodiments the controller includes a handle (not shown) and a knob (not shown). The handle has a lumen (not shown) extending longitudinally therethrough. A rod (not shown) coupled to the knob extends through the lumen and longitudinally slides within the lumen to move the rod and the knob concentrically and/or longitudinally relative to the handle. By longitudinally sliding and/or rotating the knob relative to the handle, apparatus 500 may be operated.

Cutting section 620 includes one or more radially expandable blades 626 for incising a mitral valve leaflet. Each blade 626 may be expanded or contracted using the controller. In the embodiment illustrated in FIGS. 9A-9H, cutting section 620 includes three radially expandable blades 626 configured to incise the mitral valve leaflet with a "T-shaped" incision. The number and configuration of the blades of apparatus 600 may be selected to achieve other desired incision patterns as described elsewhere herein. Each blade 626 is constructed in one-piece from a sterilized or sterilisable memory material, such as a memory metal alloy including (but not limited to) stainless steel and/or nickel and/or titanium and/or nitinol. Each bade 626 retains a pre-deformed shape in the expanded position shown in FIGS. 9E-9H. Each blade 626 is deformable into the collapsed position shown in FIGS. 9A-9D.

To expand and collapse blades 626, cutting section 620 includes a runner 670. A proximal end 626*a* of each blade 626 is coupled to runner 670. A distal end 626*b* of each blade 626 is coupled to guidewire 630. Runner 670 defines a lumen (not shown) extending longitudinally therethrough. Runner 670 is rotatably mounted about a rod 628. In some embodiments runner 670 is rotatably and slideably mounted to rod 628. Rod 628 extends from the controller through the lumen of runner 670 to permit the runner to rotate concentrically about rod 628 and/or slide longitudinally across rod 628. Runner 670 is coupled to a distal end 629a of a tube 629 for operating cutting section 620. Tube 629 is coupled to handle 116 of the controller for sliding runner 670 along rod 628 by pulling or pushing knob 118. Tube 629 defines a lumen (not shown) extending longitudinally therethrough. Rod 628 extends through the lumen of tube 629.

Figure 9A:
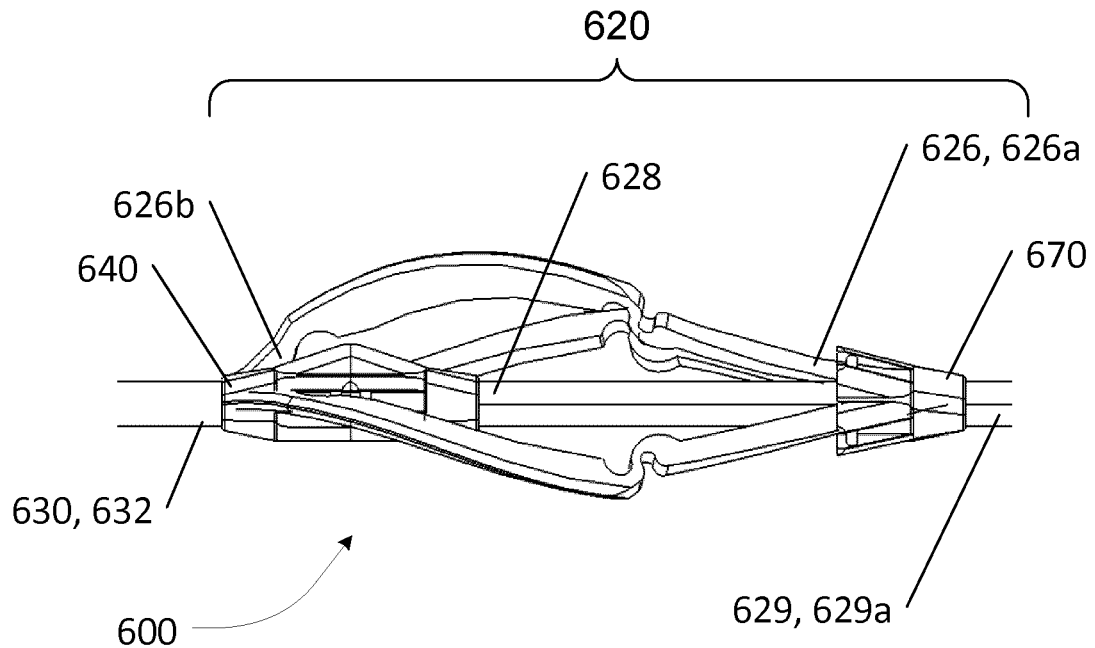
FIG. 9A is a partial side elevation view of an apparatus for use in replacing a mitral valve in a collapsed position according to an example embodiment of the present invention.
Figure 9B:
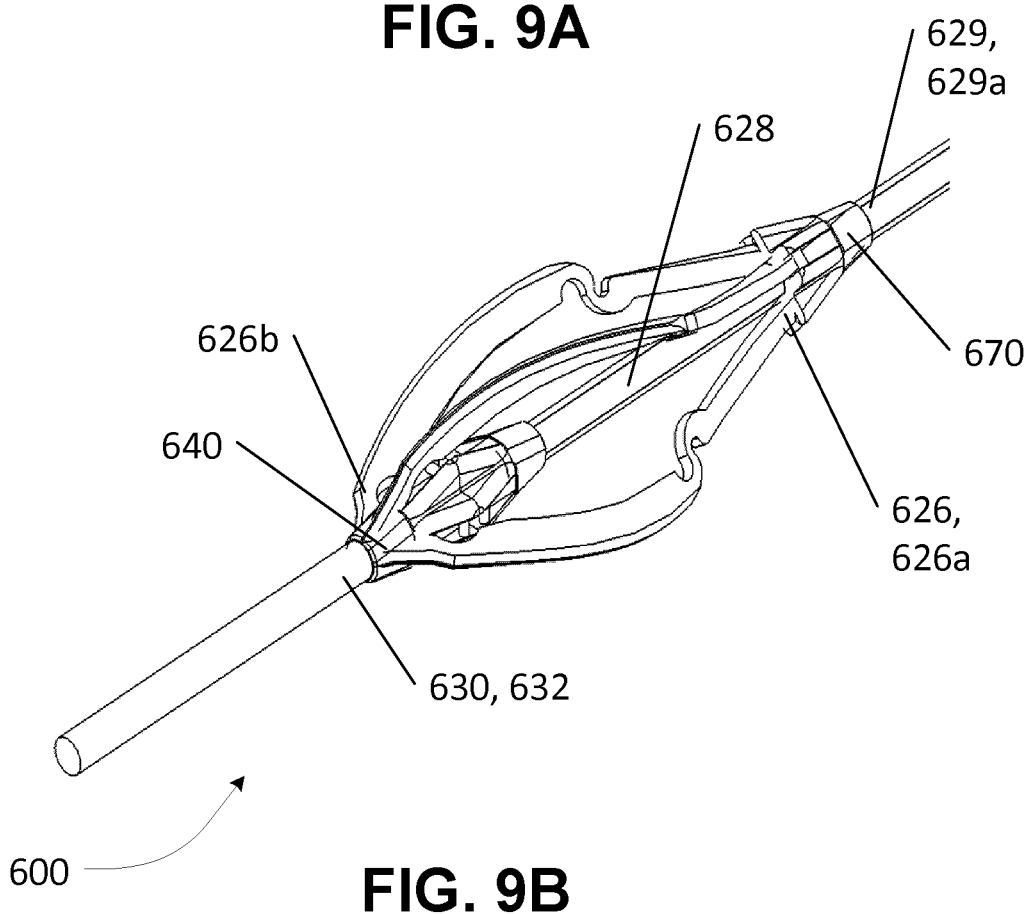
FIG. 9B is a partial front, top, side perspective view of the apparatus shown in FIG. 9A in the collapsed position.
Figure 9E:
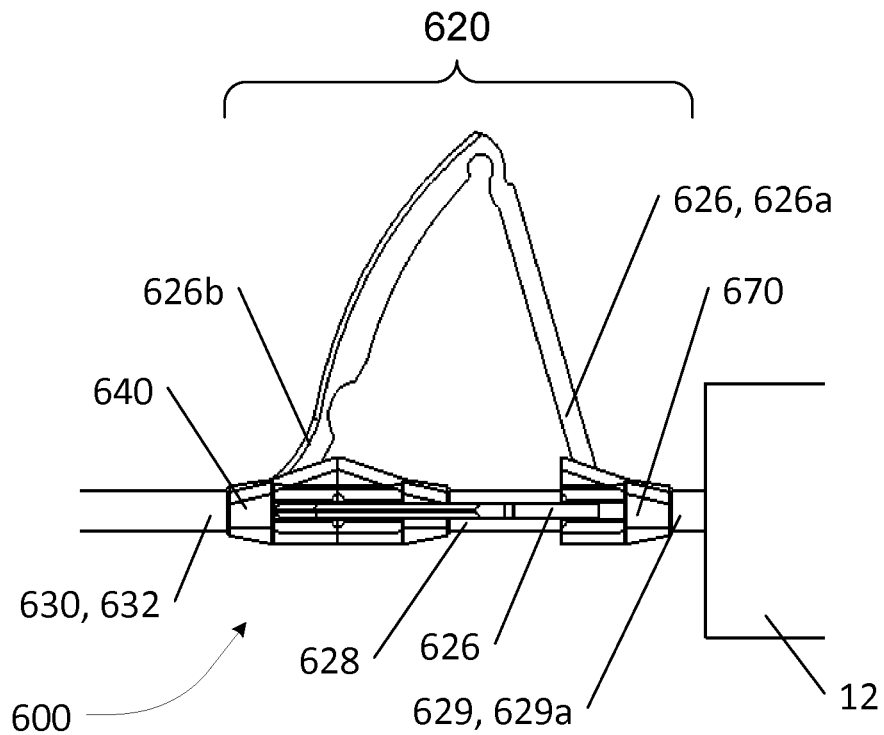
FIG. 9E is a partial side elevation view of the apparatus shown in FIG. 9A withdrawn from a catheter in a expanded position.
Figure 9F:
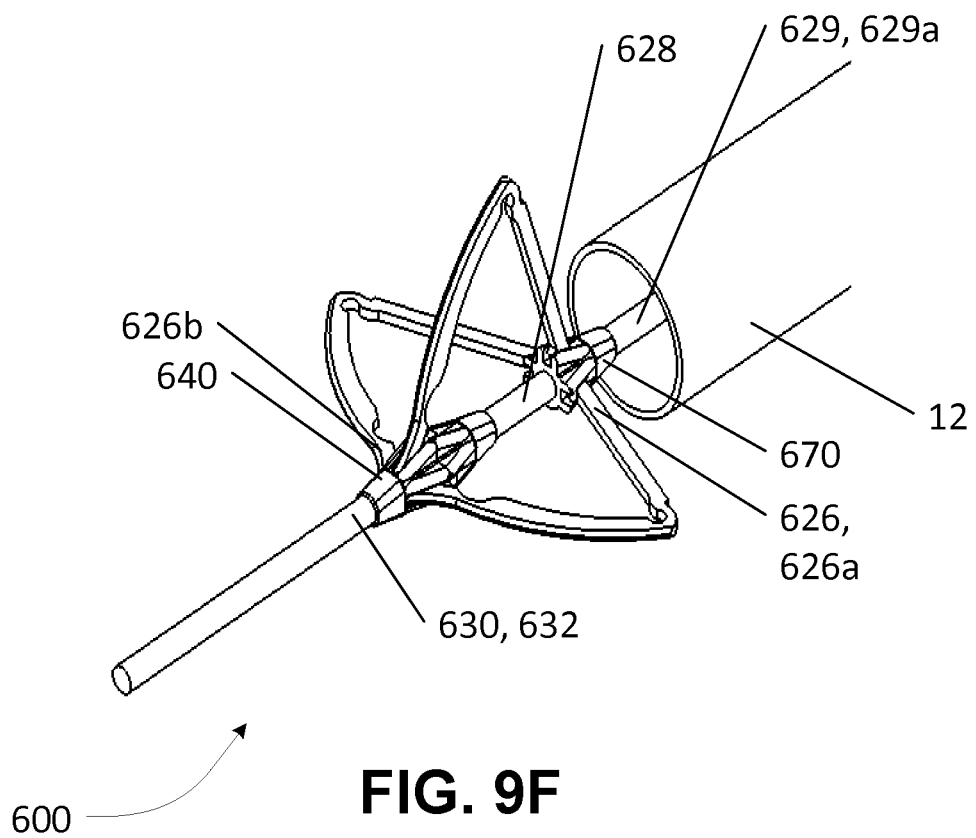
FIG. 9F is a partial front, top, side perspective view of the apparatus shown in FIG. 9A withdrawn from the catheter in the expanded position.
Figure 9H:
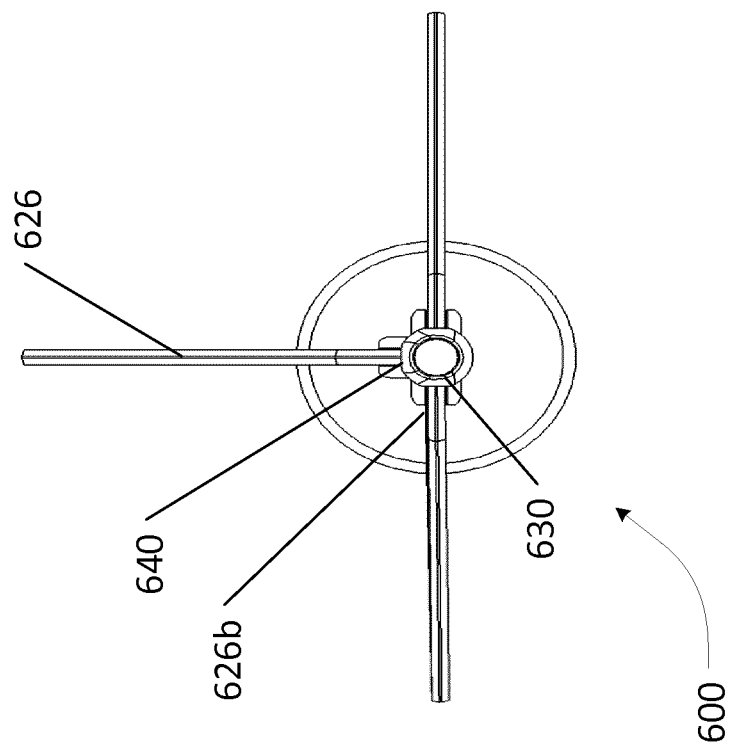
FIG. 9H is a front elevation view of the apparatus shown in FIG. 9A in the expanded position.
Figure 9G:
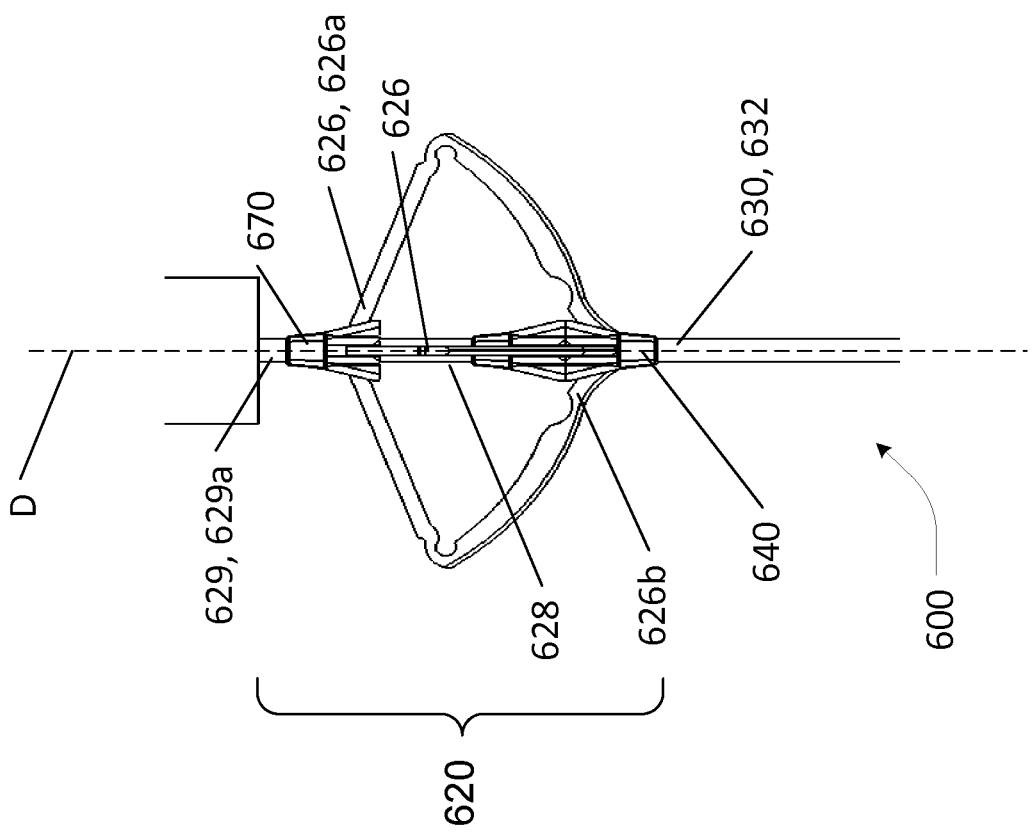
FIG. 9G is top elevation view of the apparatus shown in FIG. 9A withdrawn from the catheter in the expanded position.

In some embodiments, apparatus 600 includes a joint 640 fixedly coupled to a proximal end 632 of guidewire 630 and a distal end 626b of each cutting blade 626 is coupled to joint 640. In some embodiments runner 670 longitudinally slides across rod 628 relative to joint 640. Each blade 626 is movable from a collapsed position (FIGS. 9A-9D) into a radially expanded position (FIGS. 9E-9H) by rotating runner 670 relative to fixed joint 640 concentrically in a first direction about an axis D defined by apparatus 600 (FIG. 9C). As tube 629 is rotated in the first direction, each blade 626 is rotatably deformed about rod 621, reducing the radial cross-sectional area of the cutting section. In the collapsed position, apparatus 600 may be inserted into a catheter (e.g. catheter 12).

By rotating tube 629 relative to fixed joint 640 concentrically in a second direction opposite the first direction about axis D, each blade 626 is returned to a pre-deformed state in the expanded position whereby the radial cross-sectional area of the cutting section is greater in the expanded position than in the collapsed position. In this position, blade 626 is oriented to incise a mitral valve leaflet as described elsewhere herein. In some embodiments, by pulling tube 629 away from fixed joint 640 along axis D (with or without rotation in the first direction), the distance between ends 626a, 626b of blade 626 increases and each blade 626 radially contracts towards axis D. To radially expand blade 626, tube 629 is pushed towards fixed joint 640 along axis D (with or without rotation in the second direction), drawing runner 670 towards joint 640. As runner 670 is pushed towards joint 640 along axis D, the distance between ends 626a, 626b of blade 626 decreases and each blade 626 radially expands away from axis D.

In some embodiments apparatus 600 and/or the parts thereof comprise a sterilized or sterilisable material. In some embodiments, apparatus 600 and/or the parts thereof comprise one or more of medical grade plastic, thermal plastic, stainless steel, metal, a metal alloy (e.g. nitinol or another nickel/titanium alloy), and titanium. Persons skilled in the art will recognize that apparatus 600 and/or the parts thereof may be made of any sterilized or sterilisable material conventionally used to manufacture tools used in heart surgery.

In the embodiment illustrated in FIGS. 10A-10D, apparatus 700 includes a cutting section 720, a guidewire 730 extending away from a distal end of cutting section 720, and a controller (not shown) extending away from a proximal end of cutting section 720 opposed to the distal end. Many features and components of the controller are similar to features and components of controller 110 described elsewhere herein. In some embodiments the controller includes a handle (not shown) and a knob (not shown). The handle has a lumen (not shown) extending longitudinally therethrough. A rod (not shown) coupled to the knob extends through the lumen and longitudinally slides within the lumen to move the rod and the knob concentrically and/or longitudinally relative to the handle. By longitudinally sliding and/or rotating the knob relative to the handle, apparatus 700 may be operated.

Cutting section 720 includes one or more radially expandable blades 726 for incising a mitral valve leaflet. Each blade 726 may be expanded or contracted using the controller. To expand and collapse blades 726, cutting section 720 includes a rotator 760 housed within a case 780. Case 780 comprises at least one slot 782, each slot 782 configured to receive a corresponding blade 726 therethrough. Each blade 726 is expandable and retractable within a corresponding slot 782 defined by case 780. In some embodiments rotator 760 is coupled to rod 129 and rotator 760 is actuated by rotating rod 129. In some other embodiments rotator 760 extends longitudinally through the controller for actuating cutting section 720 by rotating rotator 760.

Figure 10A:
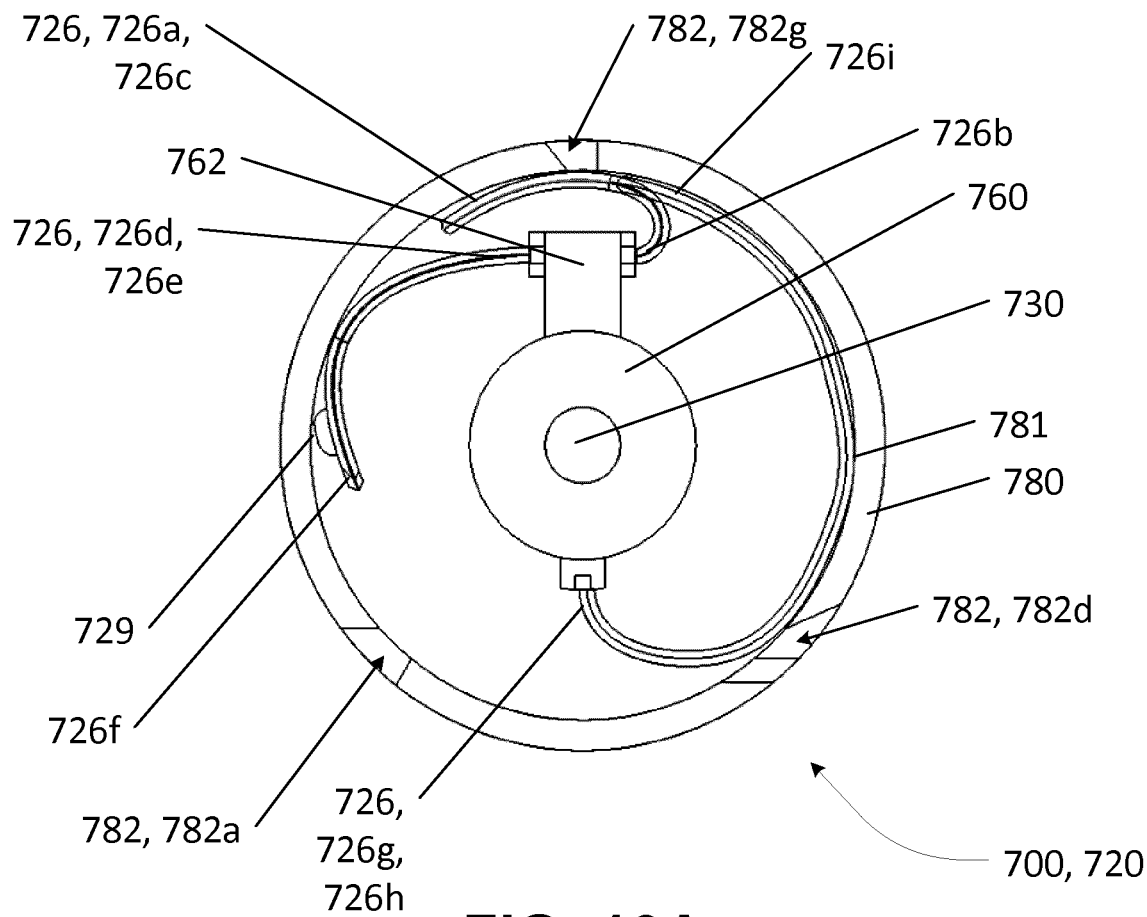
FIG. 10A is a front elevation cross-sectional view of an apparatus for use in replacing a mitral valve in a collapsed position according to an example embodiment of the present invention.

In the embodiment illustrated in FIGS. 10A-10D, cutting section 720 includes three radially expandable blades 726a, 726d, 726g configured to incise the mitral valve leaflet with a "T-shaped" incision (FIG. 10C). The number and configuration of the blades of apparatus 700 may be selected to achieve other desired incision patterns as described elsewhere herein. Each blade 726 is constructed in one-piece from a sterilized or sterilisable memory material, such as a memory metal alloy including (but not limited to) stainless steel and/or nickel and/or titanium and/or nitinol. Each bade 726 retains a pre-deformed shape in the expanded position shown in FIGS. 10C-10D. Each blade 726 is deformable into the collapsed position shown in FIGS. 10A-10B by operating rotator 760. In some embodiments one or more blades 726 are solid in construction. In some other embodiments one or more blades 726 comprise one or more openings (not shown) to permit deformation within case 780, while maintaining a desirable shape and mount of force to incise a heart valve leaflet.

Figure 10B:
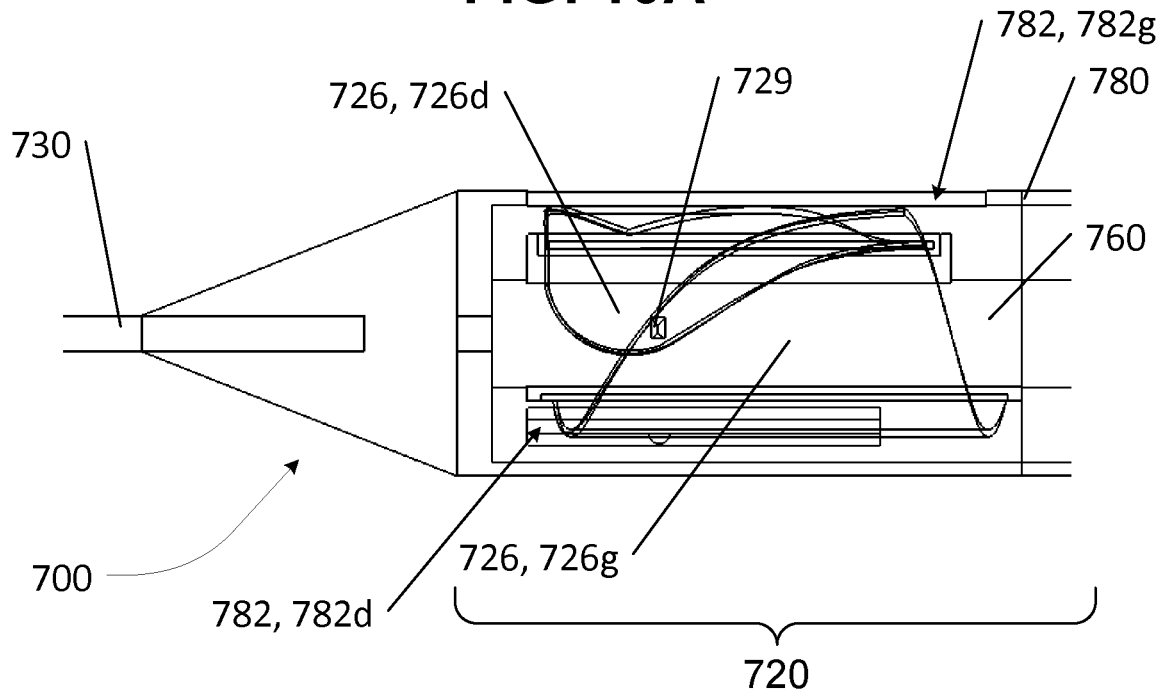
FIG. 10B is a partial side elevation cross-sectional view of the apparatus show in FIG. 10A in the collapsed position.

To provide the "T-shaped" incision pattern, a first end 726b of blade 726a is attached to an arm 762 coupled to and extending radially away from rotator 760. A first end 726e of blade 726d is attached to arm 762 so that ends 726b, 726e are coupled to opposed sides of arm 762. A first end 726h of blade 726g is coupled to rotator 760. In some embodiments, end 726h is coupled to rotator 760 at a position that is substantially opposed to arm 762 about the diameter of rotator 760. Blades 726a, 726d extend from arm 762 and wrap concentrically about an inside surface 781 of case 780 in a first direction (i.e. in the counter-clockwise direction in FIG. 10A). Blade 726g extends from rotator 760 and wraps concentrically about inside surface 781 in the first direction. With blades 726a, 726d, 726g wrapped concentrically about inside surface 781, cutting section 720 of apparatus 700 is in a collapsed position (FIGS. 10A-10B).

Cutting section 720 is movable from the collapsed position (FIGS. 10A-10B) into a radially expanded position (FIGS. 10C-10D) by rotating rotator 760 in the first direction. Ends 726c, 726f, 726i of blades 726a, 726d, 726g move concentrically about inside surface 781 of case 780 in the first direction and advance through slots 782. In some embodiments to provide the "T-shaped" incision pattern, blade 726d comprises a wedge 729 coupled adjacent to end 726f. Wedge 729 contacts inside surface 781 as blade 726d moves concentrically inside case 780. As rotator 760 is rotated in the first direction, wedge 729 prevents blade 726d from advancing through slot 782a. Wedge 729, however, does not prevent blade 726d from advancing through slot 782d. In this way, blade 726a advances through slot 782a, blade 726d advances through slot 782d, and blade 726g advances through slot 782g (FIG. 10C). To retract blade(s) 726 back through slot(s) 782, rotator 760 is rotated in a second direction (i.e. in the clockwise direction in FIG.

10A), wrapping each blade 726 concentrically about inside surface 781 of case 780 (FIG. 10A).

In some embodiments apparatus 700 and/or the parts thereof comprise a sterilized or sterilisable material. In some embodiments, apparatus 700 and/or the parts thereof comprise one or more of medical grade plastic, thermal plastic, stainless steel, metal, a metal alloy (e.g. nitinol or another nickel/titanium alloy), and titanium. Persons skilled in the art will recognize that apparatus 700 and/or the parts thereof may be made of any sterilized or sterilisable material conventionally used to manufacture tools used in heart surgery.

A method for replacing a mitral valve of a heart according to an example embodiment is shown in FIGS. 11A-11G and 12A-12J. The features and parts of the heart are similar to features and parts of heart 10, with the same reference numerals being used to indicate features and parts that are similar. The method shown in FIGS. 12A-12J demonstrates the use of apparatus 100. Apparatus 500, 600, 700 are deployed similarly as described elsewhere herein.

To replace a mitral valve, apparatus 100, 500, 600, 700 is inserted into first access site 106 of a subject and advanced using a transcatheter approach conventionally known. Apparatus 100, 500, 600, 700 may be inserted using a subaortic introducer. As described elsewhere herein, guidewire 130, 530, 630, 730 may define a hook 136 at a distal end 134 thereof. Distal end 134 may be "J-shaped" to avoid damaging heart tissue, while retaining a sharp tip to puncture a heart valve leaflet. The subaortic introducer must maintain guidewire 130, 530, 630, 730 in a linear position as apparatus 100, 500, 600, 700 is advanced through the subject's circulatory system, but must permit distal end 134 of guidewire 130, 530, 630, 730 to deform into a J-shaped configuration defining hook 136 as guidewire 130, 530, 630, 730 exits the subaortic introducer. To do so, the subaortic introducer may comprise a tip constructed from a material that may be stretched and/or torn by applying a force to distal end 134 of guidewire 130, 530, 630, 730. In some embodiments, the tip is constructed from a rigid material defining one or more points of weakness to advance guidewire 130, 530, 630, 730 therefrom. In some embodiments apparatus 100, 500, 600, 700 may be inserted using a conventional subaortic introducer (e.g. subaortic introducer 12) (FIGS. 11A and 12A) or other device considered to be within the knowledge of persons skilled in the art of interventional cardiology.

Figure 11A:
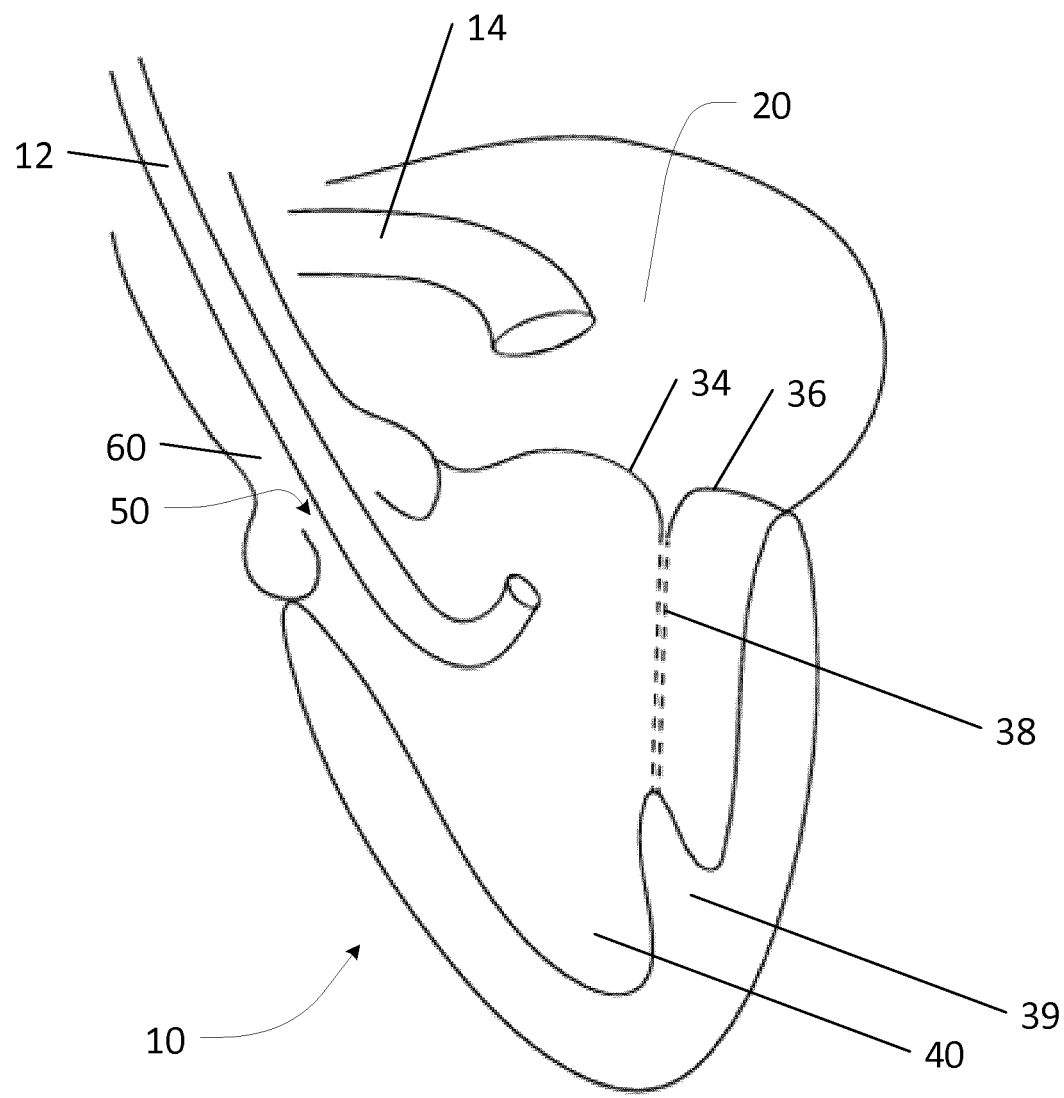
FIG. 11A is a side elevation cross-sectional view of a heart having a first catheter advanced to a left atrium of the heart and a second catheter advanced to a left ventricle of the heart.
Figure 11B:
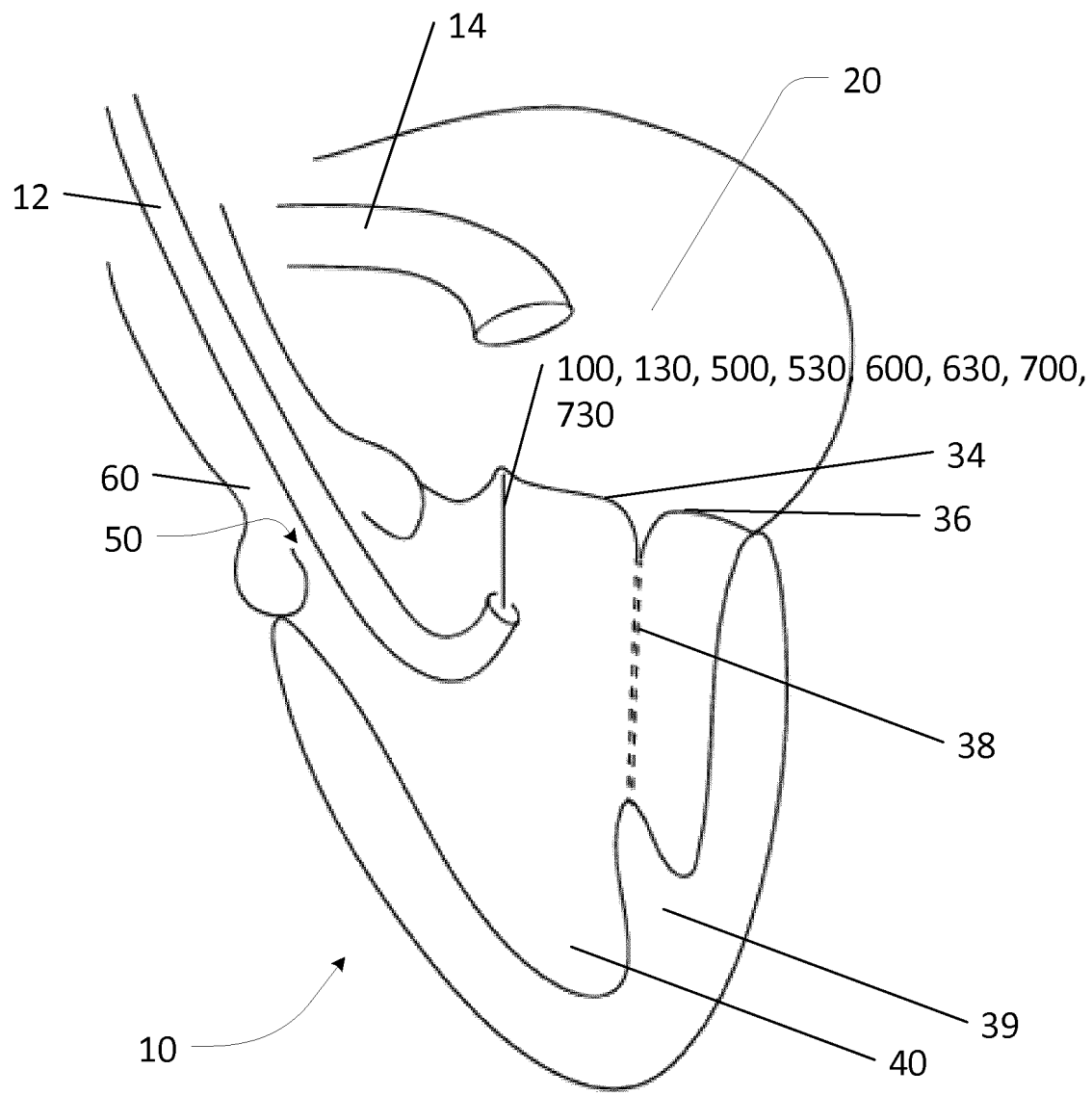
FIG. 11B is a side elevation cross-sectional view of the heart shown in FIG. 11A having an apparatus for use in replacing a mitral valve according to an example embodiment of the present invention advanced to a ventricular surface of an anterior mitral valve leaflet of the heart.

In some embodiments apparatus 100, 500, 600, 700 is advanced through introducer 14 using an antegrade transcatheter approach. In some other embodiments, apparatus 100, 500, 600, 700 is advanced through introducer 12 using a retrograde transcatheter approach. Where apparatus 100, 500, 600, 700 is introduced into a subject's femoral artery, guidewire 130, 530, 630, 730 is advanced through introducer 12 intravascularly through the artery and through an aortic valve to retroflex towards a ventricular surface of anterior leaflet 34 of mitral valve 30 (FIGS. 11B and 12A). Guidewire 130, 530, 630, 730 is punctured and advanced through the anterior leaflet (FIGS. 11C and 12B) at a location determined using conventional Transesophageal Echocardiography (TEE) and/or fluoroscopy techniques. As described elsewhere herein, the location of the guidewire puncture through anterior leaflet 34 defines the location through which cutting section 120, 520, 620, 720 will be advanced, and so guidewire 130, 530, 630, 730 is used to define the location where a transcatheter heart valve prosthesis will ultimately be implanted. In some embodiments the location of the guidewire puncture is selected so that anterior displacement of the anterior leaflet is minimized when a transcatheter heart valve prosthesis is implanted. In this way, LVOT obstruction may be avoided or minimized. In some embodiments the location of the guidewire puncture is along a central axis of the anterior leaflet at a position away from the anterior annulus so that an adequate amount of anterior leaflet tissue is available for hemostatic implantation of a transcatheter heart valve prosthesis within a docking device (not shown) and LVOT obstruction may be avoided or minimized.

Figure 11C:
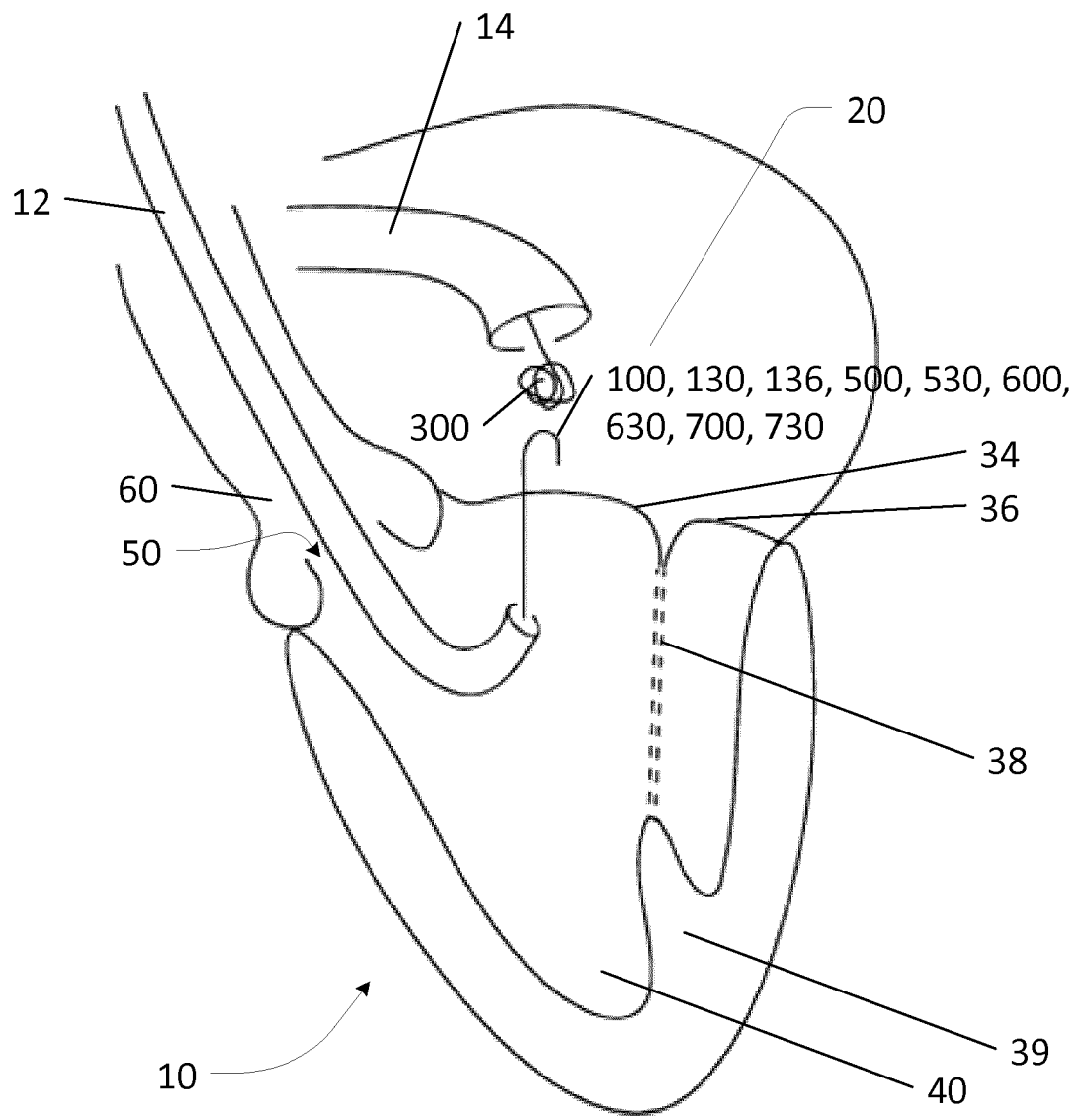
FIG. 11C is a side elevation cross-sectional view of the heart and apparatus shown in FIG. 11B, wherein a snare is advanced through the first catheter into the left atrium of the heart and a guidewire of the apparatus is advanced through the anterior mitral valve leaflet into the left atrium of the heart.
Figure 11D:
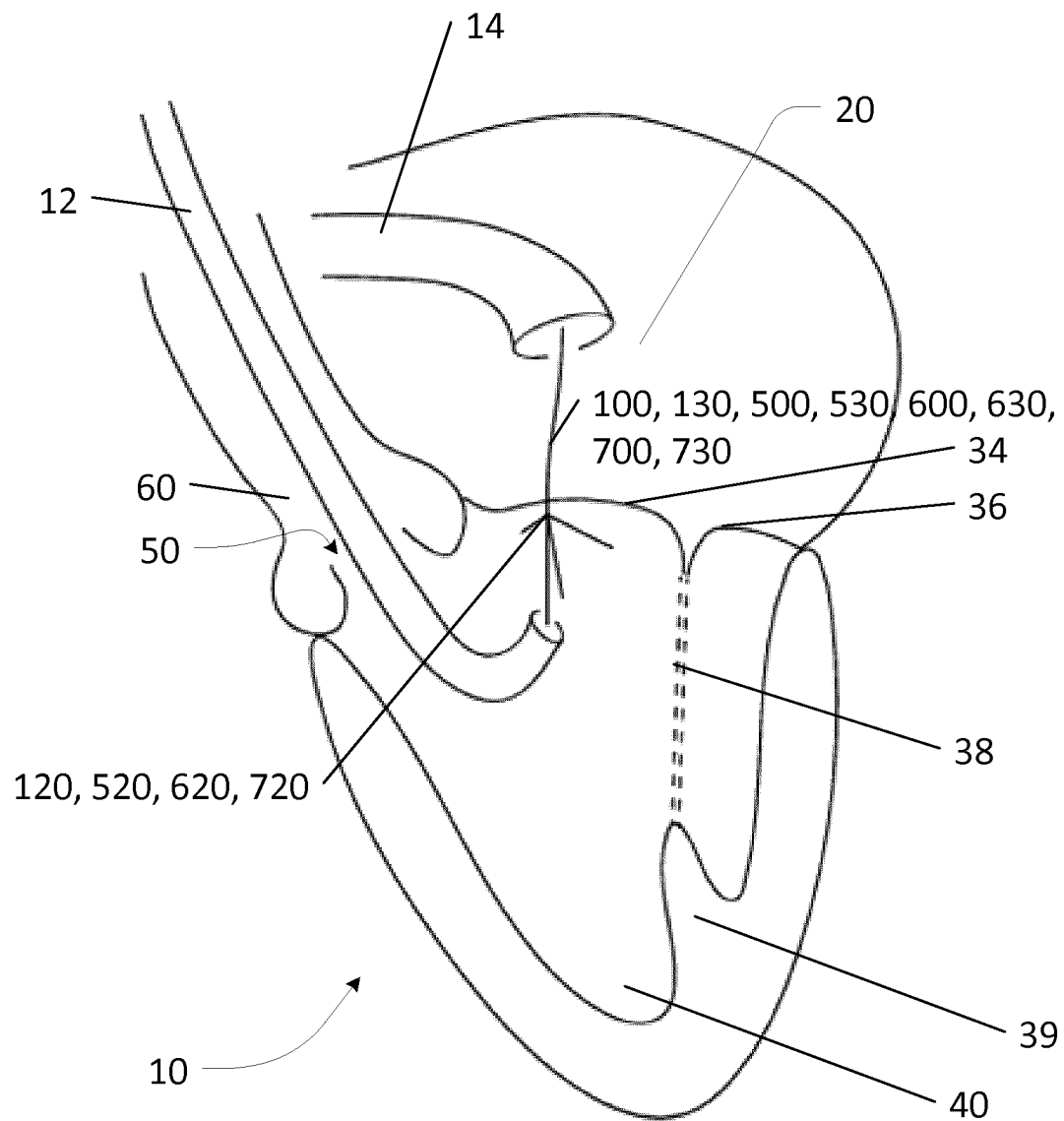
FIG. 11D is a side elevation cross-sectional view of the heart and apparatus shown in FIG. 11B, wherein a cutter of the apparatus is advanced to the ventricular surface of the anterior mitral valve leaflet of the heart.
Figure 11E:
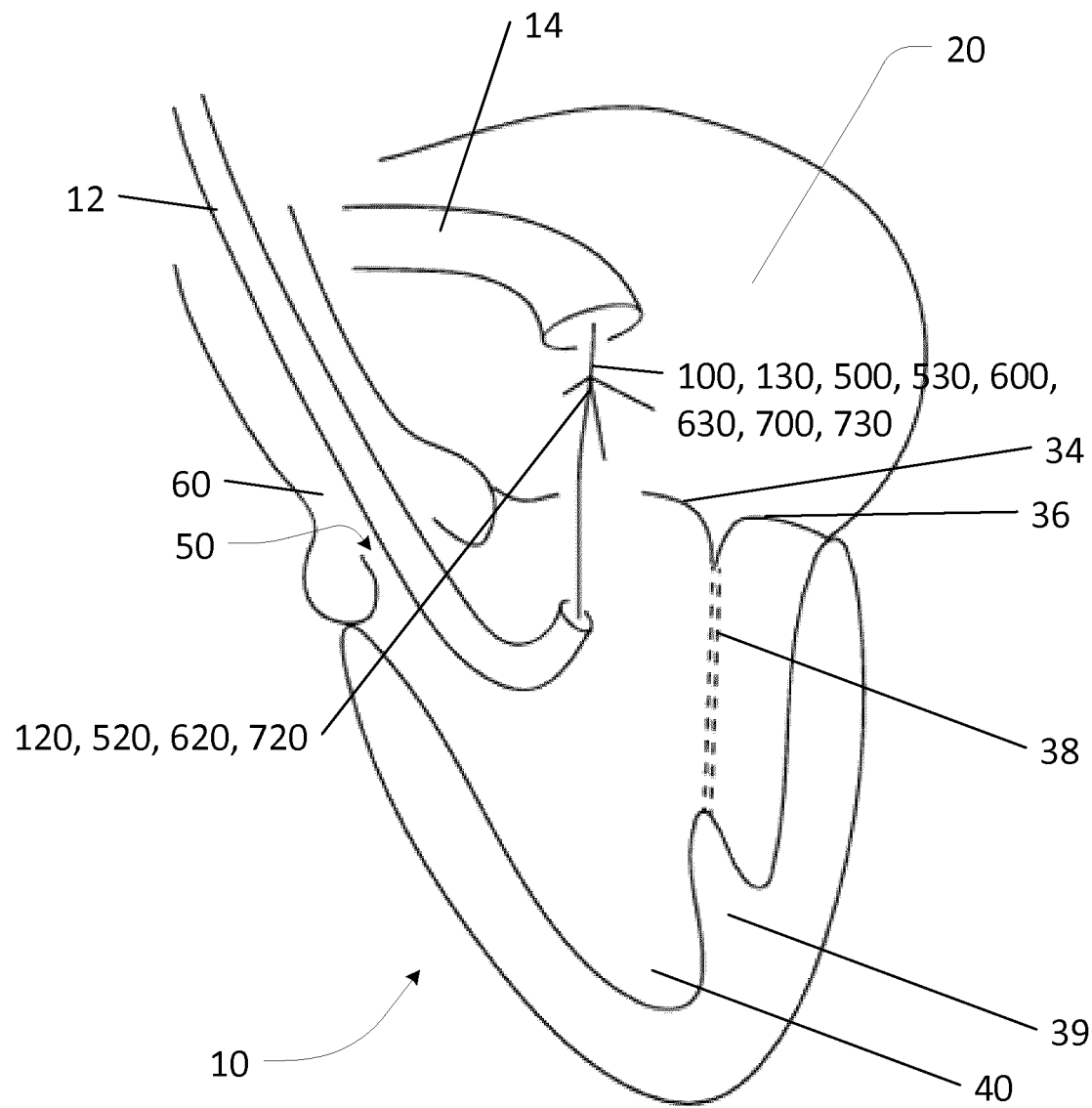
FIG. 11E is a side elevation cross-sectional view of the heart and apparatus shown in FIG. 11B, wherein the cutter of the apparatus is advanced through the anterior mitral valve leaflet into the left atrium of the heart.

In the left atrium, guidewire 130, 530, 630, 730 is snared by a snaring guidewire 300 as is conventionally known and traversed through the femoral vein to exit the subject's circulatory system at second access site 108 (FIGS. 11C and 12B). Snaring guidewire 300 is introduced into the femoral vein via second access site 108 using an antegrade transcatheter approach conventionally known. For example, snaring guidewire 300 may be inserted using a conventional transseptal introducer (e.g. transseptal introducer 14) or other device considered to be within the knowledge of persons skilled in the art of interventional cardiology. Snaring guidewire 300 is advanced through the femoral vein, through an atrial septum, to a left atrium of the subject's heart. Snaring guidewire 300 is positioned to face an atrial surface of anterior mitral valve leaflet 34. Snaring guidewire 300 snares distal end 134 of guidewire 130, 530, 630, 730 and withdraws guidewire 130, 530, 630, 730 through the subject's atrial septum. Guidewire 130, 530, 630, 730 and snaring guidewire 300 exit the subject's circulatory system through second access site 108 via the femoral vein. As guidewire 130, 530, 630, 730 is withdrawn through second access site 108 via the femoral vein, cutting section 120, 520, 620, 720 is advanced in a collapsed position through the subject's femoral artery and may be positioned adjacent the ventricular surface of anterior mitral valve leaflet 34 (FIGS. 11D and 12D). For apparatus 100, 500, 600, 700, guidewire 130, 530, 630, 730 is coupled to corresponding cutting section 120, 520, 620, 720 and, accordingly, as guidewire 130, 530, 630, 730 is withdrawn through second access site 108, corresponding cutting section 120, 520, 620, 720 is simultaneously advanced in the collapsed position through the subject's femoral artery and positioned adjacent the ventricular surface of anterior mitral valve leaflet 34.

Before the anterior mitral valve leaflet is incised, a compressed transcatheter heart valve prosthesis 400 (conventionally known) and its delivery system 16 may be passed over guidewire 130, 530, 630, 730 and introduced into the femoral vein via second access site 108 to be positioned in the subject's heart (FIGS. 12C and 12D). In this way, prosthesis 400 is ready to be advanced into a precise implant location closely or immediately following incision of the anterior leaflet by cutting section 120, 520, 620, 720 as described elsewhere herein.

As shown in FIGS. 12C-12D, with guidewire 130, 530, 630, 730 extending through anterior mitral valve leaflet 34, cutting section 120, 520, 620, 720 is advanced in a collapsed position to the ventricular surface of the anterior mitral valve leaflet. With prosthesis 400 positioned over guidewire 130, 530, 630, 730 inside the left atrium, prosthesis 400 is deliverable along guidewire 130, 530, 630, 730 to the incision site closely following incision. To incise the anterior leaflet, cutting section 120, 520, 620, 720 is deployed into an expanded position as described elsewhere herein and is advanced through the anterior leaflet incising the leaflet (FIGS. 11D-11E, and 12E-12H).

Figure 11F:
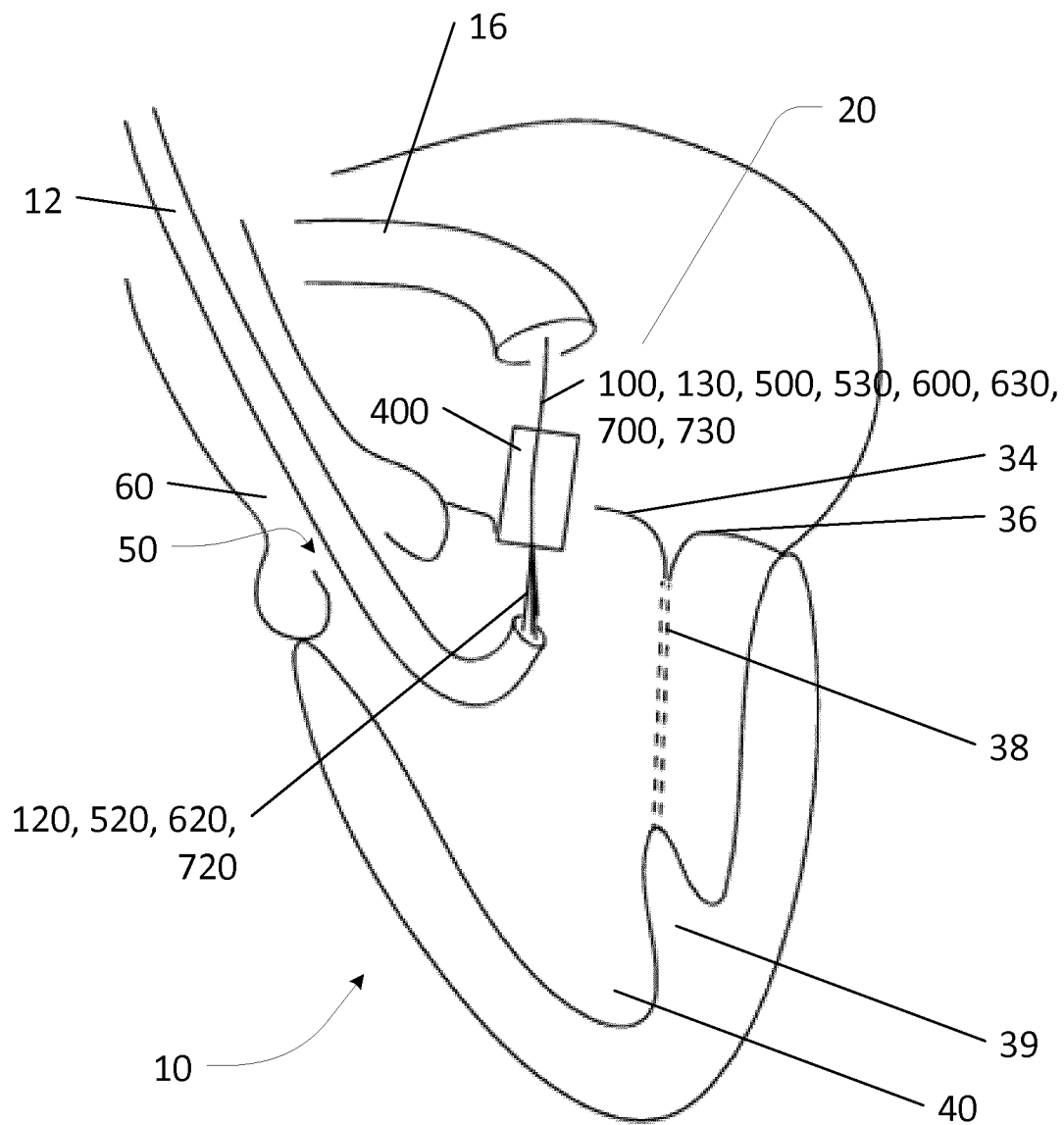
FIG. 11F is a side elevation cross-sectional view of the heart and apparatus shown in FIG. 11B, wherein a transcatheter heart valve prosthesis is advanced over the guidewire component of the apparatus and delivered to an incision in the anterior mitral valve leaflet of the heart.
Figure 11G:
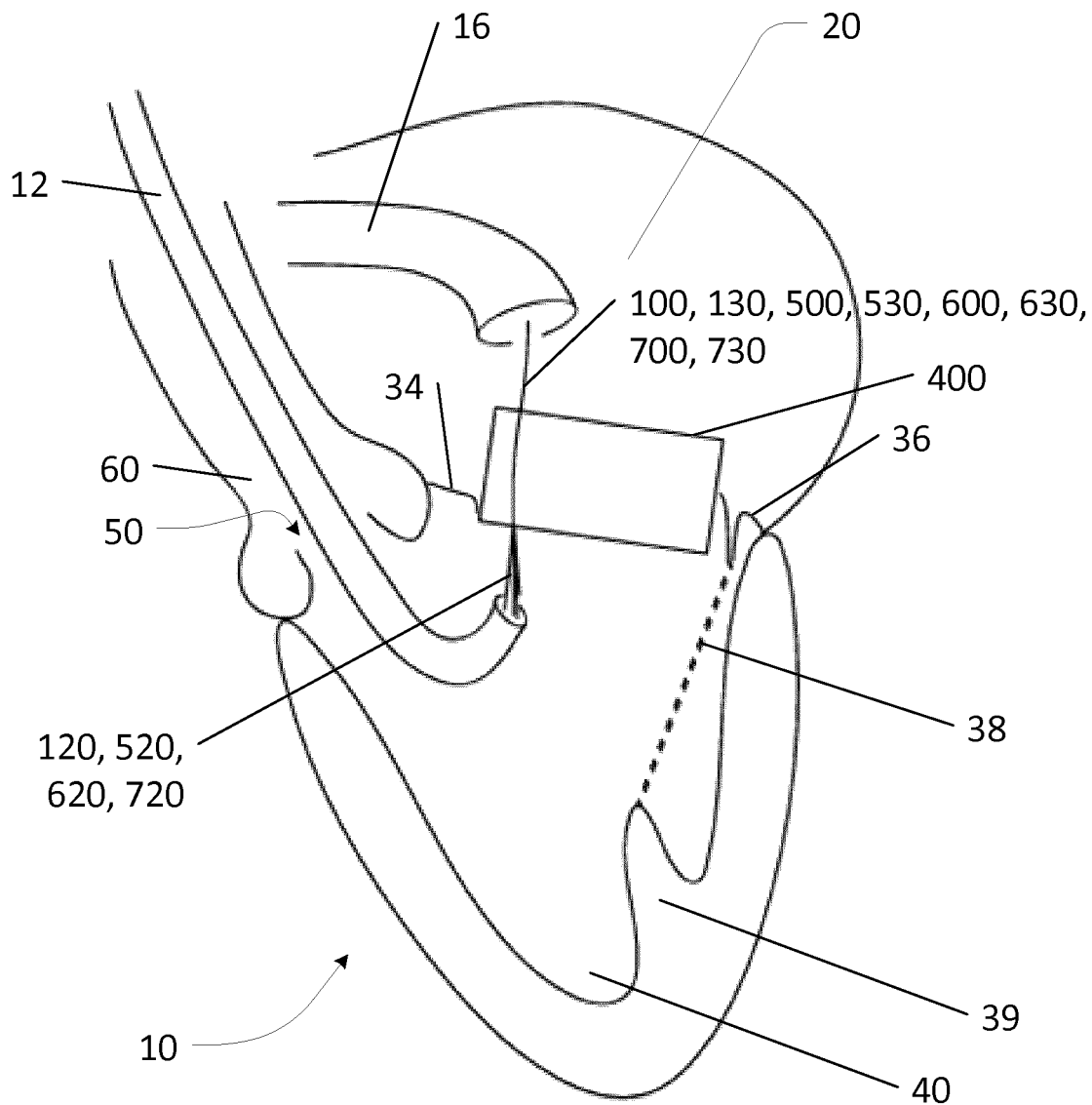
FIG. 11G is a side elevation cross-sectional view of the heart, apparatus, and transcatheter heart valve prosthesis shown in FIG. 11F, wherein the transcatheter heart valve prosthesis is positioned in the incision in the anterior mitral valve leaflet of the heart to replace the functioning of the mitral valve.
Figure 12I:
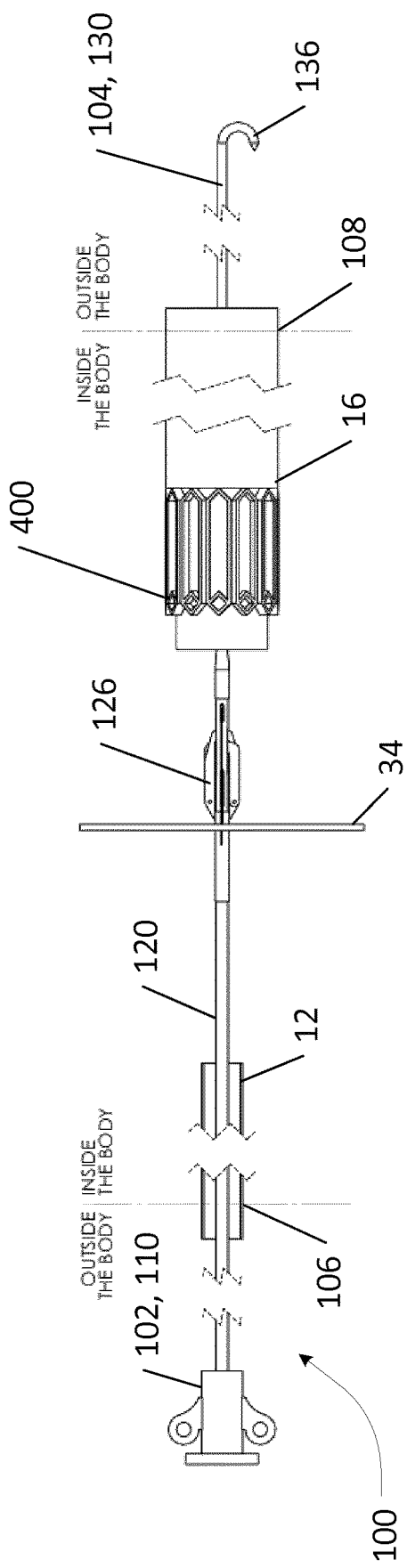
FIG. 12I is a schematic illustration of the subject's body, heart, and apparatus shown in FIG. 12C, wherein the cutter of the apparatus is collapsed in the left atrium of the heart.
Figure 12J:
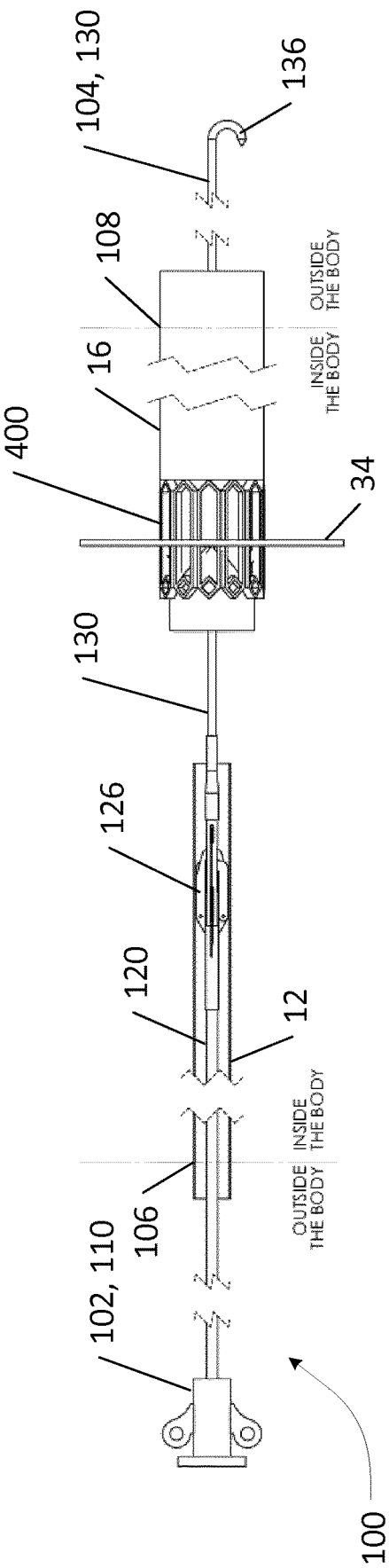
FIG. 12J is a schematic illustration of the subject's body, heart, and apparatus shown in FIG. 12C, the cutter of the apparatus is retracted through the anterior mitral valve leaflet into the second catheter and the transcatheter heart valve prosthesis is advanced into the incision in the anterior mitral valve leaflet.

After incising anterior mitral valve leaflet 34, cutting section 120, 520, 620, 720 is collapsed into the collapsed position and withdrawn through the incision into the left ventricle (FIG. 12I). Prosthesis 400 is then advanced over guidewire 130, 530, 630, 730 and positioned within the incision (FIGS. 11F and 12J). As shown in FIGS. 11E-11F and 12I-12J, closely following incision and after cutting section 120, 520, 620, 720 has been withdrawn into the left ventricle, prosthesis 400 may be delivered to the incision via guidewire 130, 530, 630, 730 and implanted therein. Prosthesis 400 is implanted as is conventionally known according to the prosthesis type. With prosthesis 400 implanted, apparatus 100, 500, 600, 700 may be withdrawn (with cutting section 120, 520, 620, 720 in a collapsed position) from the subject through first access site 106 via the femoral artery. Prosthesis 400 replaces the function of the mitral valve.

The location of the guidewire puncture through the anterior leaflet defines both the incision site (i.e. the location through which cutting section 120, 520, 620, 720 is advanced to incise the anterior leaflet) and the implant site (i.e. the location where the valve prosthesis is delivered and implanted in the anterior leaflet). In this way, anterior displacement of the anterior leaflet may be minimized when the valve prosthesis is implanted and LVOT obstruction may be avoided or minimized.

Persons skilled in the art will recognize that the method of the present invention may be modified so that apparatus 100, 500, 600, 700 is inserted through a first access site and advanced through a subject's femoral vein using an antegrade transcatheter approach conventionally known. Where apparatus 100, 500, 600, 700 is introduced into a subject's femoral vein, guidewire 130, 530, 630, 730 is advanced through the femoral vein into the left atrium of the subject's heart. Guidewire 130, 530, 630, 730 then punctures and is advanced through the anterior leaflet at a precise location as described elsewhere herein. In the left ventricle, guidewire 130, 530, 630, 730 is snared by snaring guidewire 300 as is conventionally known and is traversed through the femoral artery to exit the subject's circulatory system at the second access site.

Snaring guidewire 300 is introduced into the femoral artery via the second access site using a retrograde transcatheter approach conventionally known. Snaring guidewire 300 is advanced through the femoral artery, through the aortic valve, and is positioned to face a ventricular surface of the anterior mitral valve leaflet. Snaring guidewire 300 snares distal end 134 of guidewire 130, 530, 630, 730 and withdraws guidewire 130, 530, 630, 730 through the subject's aortic valve. Guidewire 130, 530, 630, 730 and snaring guidewire 300 exit the subject's circulatory system through the second access site via the femoral artery.

Before the anterior mitral valve leaflet is incised, prosthesis 400 and its delivery system may be passed over guidewire 130, 530, 630, 730 and introduced into the femoral artery via the second access site to be positioned in the subject's heart. Cutting section 120, 520, 620, 720 is advanced in a collapsed position to the left atrium surface of the anterior mitral valve leaflet. With prosthesis 400 positioned over guidewire 130, 530, 630, 730 inside the left ventricle, prosthesis 400 is deliverable along guidewire 130, 530, 630, 730 to the incision site closely or immediately following incision as described elsewhere herein. To incise the anterior leaflet, cutting section 120, 520, 620, 720 is deployed into an expanded position as described elsewhere herein and is advanced through the anterior leaflet incising the leaflet. As cutting section 120, 520, 620, 720 is withdrawn, prosthesis 400 is advanced over guidewire 130, 530, 630, 730 and positioned within the incision as described elsewhere herein. Apparatus 100, 500, 600, 700 may then be withdrawn (with cutting section 120, 520, 620, 720 in a collapsed position) from the subject through the first access site via the femoral vein.

Each of cutting sections 120, 520, 620, 720 and guidewires 130, 530, 630, 730 can have various lengths between corresponding proximal and distal ends. The length of apparatus 100, 500, 600, 700 is selected to intravascularly traverse a subject's circulatory system from a first access site to a second access site. In some embodiments the length of apparatus 100, 500, 600, 700 is selected to intravascularly traverse a subject's circulatory system from a first access site, through the femoral artery, through the aortic valve to the left ventricle, through the mitral valve to the left atrium, and through the femoral vein to a second access site such that the controller (e.g. controller 110) and distal end 134 of guidewire 130, 530, 630, 730 are external to the subject. The relative lengths of cutting section 120, 520, 620, 720 and guidewire 130, 530, 630, 730 may be selected depending on the identity of the first and second access sites. For example, where apparatus 100, 500, 600, 700 is introduced into a subject's circulatory system via the femoral artery, the length of guidewire 130, 530, 630, 730 is sufficient to traverse the subject's circulatory system from the anterior leaflet to a femoral vein puncture (i.e. the second access site) and to advance a conventional transcatheter heart valve prosthesis over distal end 134 external the subject's body using a conventional transcatheter valve delivery system. The length of cutting section 120, 520, 620, 720 is sufficient to traverse the subject's circulatory system from a femoral artery puncture (i.e. the first access site) to the anterior leaflet. Where apparatus 100, 500, 600, 700 is introduced into a subject's circulatory system via the femoral vein, the length of guidewire 130, 530, 630, 730 is sufficient to traverse the subject's circulatory system from a femoral artery puncture (i.e. the second access site) to the anterior leaflet and to advance a conventional transcatheter heart valve prosthesis over distal end 134 external the subject's body using a conventional transcatheter valve delivery system. The length of cutting section 120, 520, 620, 720 is sufficient to traverse the subject's circulatory system from the anterior leaflet to a femoral vein puncture (i.e. the second access site). In some embodiments the length of guidewire 130, 530, 630, 730 is approximately at least twice the length of a conventional transcatheter valve delivery system. The femoral artery may be favored in some embodiments as the first access site for one or more of its size, ease of insertion, and least tortuous path to the heart.

In some embodiments the methods and apparatus of the present invention may include one or more catheters (for example, catheter 12 and/or 14 (FIGS. 11A-12J)) for advancing apparatus 100, 500, 600, 700 through a subject's circulatory system. The catheter may be sized and dimensioned to house apparatus 100, 500, 600, 700 and/or parts thereof, and/or snaring guidewire 300, and/or a compressed transcatheter heart valve prosthesis 400 and/or its delivery system intravascularly. In some embodiments the methods and apparatus of the present invention may include one or more transcatheter valve delivery systems (for example, transcatheter valve delivery system 16 (FIGS. 12C-12D, 12E, and 12G-12J) for advancing transcatheter heart valve prosthesis 400 through a subject's circulatory system. The transcatheter valve delivery system may be sized and dimensioned to house prosthesis 400 and/or parts thereof intravascularly.

Transcatheter mitral and aortic valve prostheses for use with the methods and apparatus of the present invention are conventionally known and include, but are not limited to, apical tethers, annular winglets, native leaflet engagement devices, radial force devices, mitral annulus clamping devices, external anchor devices, and annular docking devices. Other transcatheter mitral and aortic valve prostheses for use with the methods and apparatus of the present invention are considered to be within the knowledge of persons skilled in the art of interventional cardiology and cardiac surgery.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof; elements which are integrally formed may be considered to be connected or coupled;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An apparatus for use in mitral valve replacement comprising:
   a controller having a longitudinally-extending controller rod;
   a cutting section coupled to a distal end of the controller rod and comprising at least one cutting blade radially expandable about a longitudinal axis of the apparatus between a radially collapsed position for delivering the apparatus to a mitral valve and a radially expanded position for incising a mitral valve leaflet, the cutting section being defined by a lumen extending longitudinally therethrough; and
   a guidewire coupled to the cutting section and extending away from a distal end of the cutting section,
   wherein the apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly,
   wherein the guidewire extends longitudinally through the lumen of the cutting section and is slideable within the lumen about the longitudinal axis of the apparatus,
   wherein the at least one cutting blade is formed from a memory material, and retains a pre-deformed shape in the expanded position and is deformable into a deformed shape in the collapsed position,
   wherein a proximal end of the at least one cutting blade is coupled to the distal end of the controller rod, and a distal end of the at least one cutting blade is coupled to a proximal end of the guidewire,
   wherein the cutting section further comprises a lever arm pivotally coupling the at least one cutting blade to the controller rod.

2. The apparatus according to claim 1, wherein the lever arm has a proximal end pivotally coupled to the distal end of the controller rod and an opposed distal end of the lever arm pivotally coupled to a proximal end of the at least one cutting blade, a distal end of the at least one cutting blade being pivotally coupled to a proximal end of the guidewire.

3. The apparatus according to claim 1, wherein the cutting section further comprises a longitudinally-extending cutting rod and a runner slideably mounted on the cutting rod, the cutting rod being connected to the distal end of the controller rod.

4. The apparatus according to claim 3, wherein the proximal end of the at least one cutting blade is coupled to the runner and the distal end of the at least one cutting blade is coupled to a fixed joint secured at the proximal end of the guidewire, the runner being longitudinally slideable about the cutting rod relative to the fixed joint.

5. An apparatus for use in mitral valve replacement comprising:
- a controller having a longitudinally-extending controller rod;
- a cutting section coupled to a distal end of the controller rod and comprising at least one cutting blade radially expandable about a longitudinal axis of the apparatus between a radially collapsed position for delivering the apparatus to a mitral valve and a radially expanded position for incising a mitral valve leaflet, the cutting section being defined by a lumen extending longitudinally therethrough; and
- a guidewire coupled to the cutting section and extending away from a distal end of the cutting section,
- wherein the apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly,
- wherein the cutting section further comprises a longitudinally-extending cutting rod and a runner slideably mounted on the cutting rod, the cutting rod being connected to the distal end of the controller rod,
- wherein the runner is rotatable about the cutting rod to rotate the at least one cutting blade about a longitudinal axis of the cutting rod.

6. The apparatus according to claim 5, wherein the guidewire extends longitudinally through the lumen of the cutting section and is slideable within the lumen about the longitudinal axis of the apparatus.

7. The apparatus according to claim 6, wherein the at least one cutting blade is formed from a memory material, and retains a pre-deformed shape in the expanded position and is deformable into a deformed shape in the collapsed position.

8. The apparatus according to claim 7, wherein a proximal end of the at least one cutting blade is coupled to the distal end of the controller rod, and a distal end of the at least one cutting blade is coupled to a proximal end of the guidewire.

9. The apparatus according to claim 5, wherein a radial cross-sectional area of the cutting section is reduced by rotating the at least one cutting blade about the longitudinal axis in a first direction, and the radial cross-sectional area of the cutting section is increased by rotating the at least one cutting blade about the longitudinal axis in a second direction opposed to the first direction.

10. An apparatus for use in mitral valve replacement comprising:
- a controller having a longitudinally-extending controller rod;
- a cutting section coupled to a distal end of the controller rod and comprising at least one cutting blade radially expandable about a longitudinal axis of the apparatus between a radially collapsed position for delivering the apparatus to a mitral valve and a radially expanded position for incising a mitral valve leaflet, the cutting section being defined by a lumen extending longitudinally therethrough; and
- a guidewire coupled to the cutting section and extending away from a distal end of the cutting section,
- wherein the apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly
- wherein the cutting section comprises a rotator housed within a case defining one or more slots configured to receive the at least one blade.

11. The apparatus according to claim 10, wherein the at least one cutting blade extends radially from the rotator and wraps concentrically about an inside surface of the case in the collapsed position.

12. The apparatus according to claim 11, wherein the at least one cutting blade is expandable and retractable within the slot.

13. The apparatus according to claim 12, wherein the at least one cutting blade extends radially from the rotator through the slot in the expanded position.

14. An apparatus for use in mitral valve replacement comprising:
- a controller having a longitudinally-extending controller rod;
- a cutting section coupled to a distal end of the controller rod and comprising at least one cutting blade radially expandable about a longitudinal axis of the apparatus between a radially collapsed position for delivering the apparatus to a mitral valve and a radially expanded position for incising a mitral valve leaflet, the cutting section being defined by a lumen extending longitudinally therethrough; and
- a guidewire coupled to the cutting section and extending away from a distal end of the cutting section,
- wherein the apparatus is sized and dimensioned to enter a subject through a first access site, traverse through at least part of a subject's circulatory system, and exit the subject through a second access site so that a distal end of the guidewire and the controller are external to the subject's circulatory system when the apparatus is situated intravascularly,
- wherein the guidewire extends longitudinally through the lumen of the cutting section and is slideable within the lumen about the longitudinal axis of the apparatus,
- wherein the at least one cutting blade is formed from a memory material, and retains a pre-deformed shape in the expanded position and is deformable into a deformed shape in the collapsed position,
- wherein a proximal end of the at least one cutting blade is coupled to the distal end of the controller rod, and a distal end of the at least one cutting blade is coupled to a proximal end of the guidewire,
- wherein the cutting section is configured to incise the mitral valve leaflet with a predetermined pattern, the predetermined pattern is selected from the group consisting of: a T-shaped incision, a linear incision, and an X-shaped incision.

15. The apparatus according to claim 14, wherein the at least one blade extends radially away from the longitudinal axis of the apparatus and in a configuration that corresponds to the predetermined pattern.

* * * * *